US007427596B2

(12) United States Patent
Keyt et al.

(10) Patent No.: US 7,427,596 B2
(45) Date of Patent: Sep. 23, 2008

(54) VARIANTS OF VASCULAR ENDOTHELIAL CELL GROWTH FACTOR, THEIR USES, AND PROCESSES FOR THEIR PRODUCTION

(75) Inventors: Bruce A. Keyt, Pacifica, CA (US); Francis Hung Nguyen, Daly City, CA (US); Napoleone Ferrara, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 179 days.

(21) Appl. No.: 11/145,494

(22) Filed: Jun. 3, 2005

(65) Prior Publication Data

US 2006/0024785 A1    Feb. 2, 2006

Related U.S. Application Data

(63) Continuation of application No. 09/346,069, filed on Jul. 1, 1999, now Pat. No. 7,005,505, which is a continuation of application No. 08/567,200, filed on Dec. 5, 1995, now Pat. No. 6,020,473.

(60) Provisional application No. 60/002,827, filed on Aug. 25, 1995.

(51) Int. Cl.
*A61K 38/18*    (2006.01)
*A61K 38/16*    (2006.01)

(52) U.S. Cl. .......................... 514/12; 530/350

(58) Field of Classification Search ..................... None
See application file for complete search history.

(56) References Cited

U.S. PATENT DOCUMENTS

| | | | |
|---|---|---|---|
| 3,691,016 A | 9/1972 | Patel | |
| 3,773,919 A | 11/1973 | Boswell et al. | |
| 3,887,699 A | 6/1975 | Yolles | |
| 3,969,287 A | 7/1976 | Jaworek et al. | |
| 4,195,128 A | 3/1980 | Hildebrand et al. | |
| 4,229,537 A | 10/1980 | Hodgins et al. | |
| 4,247,642 A | 1/1981 | Hirohara et al. | |
| 4,330,440 A | 5/1982 | Ayers | |
| 4,399,216 A | 8/1983 | Axel et al. | |
| 5,073,492 A | 12/1991 | Chen et al. | |
| 5,219,739 A | 6/1993 | Tischer et al. | |
| 5,332,671 A | 7/1994 | Ferrara et al. | |
| 5,607,918 A | 3/1997 | Eriksson et al. | |
| 6,057,428 A | 5/2000 | Keyt et al. | |
| 6,750,044 B1 * | 6/2004 | Keyt et al. | |
| 7,090,834 B1 * | 8/2006 | Cunningham et al. | |
| 2006/0063203 A1 * | 3/2006 | Cunningham et al. | |
| 2007/0142284 A1 * | 6/2007 | Cunningham et al. | |

FOREIGN PATENT DOCUMENTS

| | | |
|---|---|---|
| CA | 1 176 565 | 10/1984 |
| EP | 0 058 481 | 8/1981 |
| EP | 0 036 776 | 9/1981 |
| EP | 0 075 444 | 3/1983 |
| EP | 0 133 988 | 3/1985 |
| EP | 0 158 277 | 10/1985 |
| EP | 0 160 457 | 11/1985 |
| EP | 0 266 032 | 5/1988 |
| EP | 0 509 477 | 9/1990 |
| WO | WO 87/05330 | 9/1987 |
| WO | WO 90/13649 | 11/1990 |

OTHER PUBLICATIONS

Strader et al., Structural basis of beta-adrenergic receptor function, FASEB J. 3:1825-1832, 1989.*
Adelman et al., 1983, *DNA*, 2(3):183-193 "In vitro Deletional Mutagenesis for Bacterial Production of the 20,000-Dalton Form of Human Pituitary Growth Hormone".
Aiello et al., 1994, *New England J of Medicine*, 331(22):1480-1487 "Vascular endothelial growth factor in ocular fluid of patients with diabetic retinopathy and other retinal disorders".
Aplin et al., 1981, *CRC Crit. Rev. Biochem.*, 10(4):259-306 "Preparation, Properties, and Applications of Carbohydrate Conjugates of Proteins and Lipids".
Aviv et al., 1972, *Proc. Natl. Acad. Sci. USA*, 69(6): 1408-1412 "Purification of Biologically Active Globin Messenger RNA by Chromatography on Oligotymidylic Acid-Cellulose".
Baenziger, 1984, In *The Plasma Proteins: Structure, Function, and Genetic Control*, F.W. Putnam, cds, 2d edition, Adademic Press: New York, vol. IV, Chapter 5, pp. 271-315 "The Oligosaccharides of Plasma Glycoproteins: Synthesis, Structure, and Function".
Barzu et al., 1985,*Biochimica et Biophysica Acta*, 845:196-203 "Binding and endocytosis of heparin by human endothelial cells in culture".
Benton et al., 1977, *Science*, 196:180-182 "Screening λgt recombinant clones by hybridization to single plaques in situ".
Bolivar et al., 1977, *Gene*, 2:95-113 "Construction and Characterization of New Cloning Vehicles. II. A Multipurpose Cloning System".
Bothwell et al., 1981, *Nature*, 290:65-67 "Dual expression of λ genes in the MOPC-315 plasmacytoma".

(Continued)

*Primary Examiner*—Lorraine Spector
*Assistant Examiner*—Claire Kaufman

(57) ABSTRACT

The present invention involves the preparation of vascular endothelial growth factor (VEGF) variants which provide materials that are selective in respect of binding characteristics to the kinase domain region and the FMS-like tyrosine-kinase region, respectively KDR and FLT-1. The respective KDR and FLT-1 receptors are bound by corresponding domains within the VEGF compound domains. The variants hereof define those two binding regions and modify them so as to introduce changes that interrupt the binding to the respective domain. In this fashion the final biological characteristics of the VEGF molecule are

OTHER PUBLICATIONS

Breir et al., 1992, *Dev.*, 114:521-532 "Expression of vascular endothelial growth factor during embryonic angiogenesis and endothelial cell differentiation".

Chang, 1978, *Nature*, 375:615 "Are World Summits Really Necessary".

Chen et al., 1987, *Mol. Cell Biol.*, 7(8):2745-2752 "High-efficiency transformation of mammalian cells by plasmid DNA".

Cohen et al., 1972, *Proc. Natl. Acad. Sci. USA*, 69(8):2110-2114 "Nonchromosomal Antibiotic Resistance in Bacteria: Genetic Transformation of *Escherichia coli* by R-Factor DNA".

Crea et al., 1978, *Proc. Natl. Acad. Sci. USA*, 75(12):5765-5769 "Chemical Synthesis of Genes for Human Insulin".

Creighton, T.E., 1983, In *Proteins: Structure and Molecular Principles*, W.H. Freeman & Co., San Francisco pp. 79-86.

Ferrara et al., 1989, *Biochem. & Biophys. Res. Comm.*, 161(2):851-858 "Pituitary Follicular Cells Secrete a Novel Heparin-binding Growth Factor Specific for Vascular Endothelial Cells".

Ferrara, N., 1995, *Laboratory Investigation*, 72(6):615-618 "Vascular endothelial growth factor. The trigger for neovascularization in the eye".

Fiers et al., 1990, *Nature*, 273:113-120 "Complete Nucleotide Sequences of SV40 DNA".

Froehler et al., 1986, *Nuceleic Acids Research*, 14(13):5399-5407 "Synthesis of DNA via Deoxynucleoside H-Phosphonate Intermediates".

George et al., 1990, *Meth. Enzymol.*, 183:333-351 "Mutation data matrix and its uses".

GenBank Database, Liang et al., Apr. 1998, Accession No. AAC41274 "vascular endothelial growth factor isoform 165 [Danio rerio]".

GenBank Database, Eichmann et al., May 1998, Accession No. CAA75799 "vascular endothelial growth factor C [Coturnix coturnix]".

GenBank Database, Cleaver et al., Jul. 1997, Accession No. AAB63680 "vascular endothelial growth factor 196 [Xenopus laevis]".

GenBank Database, Junqueira de Azevedo, et al., Oct. 2001, Accession No. AAK52103 "vascular endothelial growth factor precursor [Bothrops jararaca]".

GenBank Database, Meyer et al., Mar. 1999, Accession No. AAD03735 "vascular endothelial growth factor homolog Vegf-c [Orf virus]".

Goeddel et al., 1979, *Nature*, 281:544-548 "Direct Expression in *Escherichia coli* of a DNA Sequence Coding for Human Growth Hormone".

Goeddel et al., 1980, *Nucleic Acids Research*, 8(18):4057-4074 "Synthesis of Human Fibroblast Interferon by *E. coli*".

Gorman et al., 1990, *DNA Prot. Eng. Tech.*, 2(1):3-10 "Transient Production of Proteins Using an Andenovirus Transformed Cell Line".

Graham et al., 1973, *Virology*, 52:456-467 "A New Technique for the Assay of Infestivity of Human Adenovirus 5 DNA".

Green et al., 1983, *Cell*, 32(3):671-694 "Human β-globin pre-mRNA synthesized in vitro is accurately spliced in Xenopus oocyte nuclei".

Haniu et al., 1993, *Biochemistry*, 32:2431-2437 "Disulfide bonds in recombinant human platelet-derived growth factor BB dimer: characterization of intermolecular and intramolecular disulfide linkages".

Hess et al., 1968, In *Advances in Enzyme Regulation*, George Weber, New York: Pergamon Press, 7:149-167 "Cooperation of Glycolytic Enzymes".

Hitzeman et al., 1980, *Journal of Biological Chemistry*, 255(24):12073-12080 "Isolation and Characterization of the Yeast 3-Phosphoglycerokinase Gene (PGK) by an Immunological Screening Technique".

Holland et al., 1978, *Biochemistry*, 17(23):4900-4907 "Isolation and Identification of Yeast Messenger Ribonucleic Acids Coding for Enolase, Glyceraldehyde-3-phosphate Dehydrogenase, and Phosphoglycerate Kinase".

Houck et al., 1992, *Journal of Biological Chemistry*, 267:26031-26037 "Dual regulation of vascular endothelial growth factor bioavailability by genetic and proteolytic mechanisms".

Hsiao et al., 1979, *Proc. Natl. Acad. Sci. USA*, 76:3829-3833 "High-frequency Transformation of Yeast by Plasmids Containing the Cloned Yeast $Arg^4$ Gene".

Hunter et al., 1962, *Nature*, 194:495-496 "Preparation of Iodine 131 Labelled Human Growth Hormone of High Specific Activity".

Huynh et al., 1985, *DNA Cloning, A Practical Approach*, D.M. Glover 1:49-78 "Constructing and Screening cDNA Libraries in λgt10 and λgt11".

Itakura et al., 1977, *Science*, 198:1056-1063 "Expression of *Escherichia Coli* of a Chemically Synthesized Gene for the Hormone Somatostatin".

Jones E., 1977, *Genetics*, 85(1):23-33 "Proteinase Mutants of Saccharomyees Cerevisiao".

Kendall et al., 1994, *Biochem. Biophys. Res.*, 201(1):326-330 "Specificity of Vascular Endothelial Cell Growth Factor Receptor Ligand Binding Domains".

Keyt et al., 1996, *Journal of Biological Chemistry*, 271(13):7788-7795 "The Carboxyl-terminal Domain (111-165) of Vascular Endothelial Growth Factor Is Critical for Its Mitogenic Potency".

Keyt et al, 1996, *Journal of Biological Chemistry*, 271(10):5638-5646 "Identification of Vascular Endothelial Growth Factor Determinants for Binding KDR and FLT-I Receptors".

Kim et al., 1992, *Growth Factors*, 7(1):53-64 "The Vascular Endothelial Growth Factor Proteins: Identification of Biologically Relevant Regions by Neutralizing Monoclonal Antibodies".

Kingsman et al., 1979, *Gene*, 7:141-152 "Replication of Saccharmoyees Cerevisiae of Plasmid pBR313 Carrying DNA from the Yeast trp1 Region".

Kukuruzinska et al., 1987, *Annu. Rev. Biochem.* 56:915-944 "Protein glycosylation in yeast".

Kunkel et al., 1987 *Methods in Enzymology*. 154:367-382 "Rapid and Efficient Site-specific Mutagenesis Without Phenotypic Selection".

Kunkel, T., 1985, *Proc. Natl. Acad. Sci. USA*, 82:488-492 "Rapid and Efficient Site-specific Mutagenesis Without Phenotypic Selection".

Langer, 1982, *Chem. Tech.*, 12:98-105 "Controlled Release of Macromolecules".

Lawn et al., 1981, *Nucleic Acids Research*, 9(22):6103-6114 "The Sequence of Human Serum Albumin cDNA and its Expression in *E. coli*".

Lusky and Botchen, 1981, *Nature*, 293:79-81 "Inhibition of SV40 replication in simian cells by specific pBR322 DNA sequences".

Maher et al., 1993, *Oncogenes*, 8:533-541 "Alanine Mutagenesis of Conserved Residues in the Platelet-Dervived Growth Factor Family: Identification of Residues Necessary for Dimerization and Tranformation".

Mandel et al., 1970, *J. Mol. Biol.*, 53:159-162 "Calcium-dependent Bacteriophage DNA Infection".

Maniatis et al., 1978, In *Molecular Cloning: A Laboratory Manual*. Cold Spring Harbor Laboratory Press: Cold Spring Harbor, New York, pp. 31, 90-91, 133-134.

Maniatis et al., 1978, *Cell*. 15:687-701 "The Isolation of Structural Genes from Libraries of Eucaryotic DNA".

Marshall, R.D., 1974, *Biochem. Soc. Symp.*, 40:17-26 "The nature and metabolism of the carbohydrate-peptide linkages of glycoproteins".

Maxam et al., *Methods in Enzymology*, 65:499-560 "Sequencing End-labeled DNA with Base-Specific Chemical Cleavages".

Messing et al., In *Proceedings of the Third Cleveland Symposium on Macromolecules: Recombinant DNA*, Walton, A., Elsevier: Amsterdam, pp. 143-153.

Messing et al., 1981, *Nucleic Acids Research*, 9(2):209-321 "A System for Shotgun DNA Sequencing".

Nakamaye et al., 1986, *Nucleic Acids Research*, 14(24):9679-9698 "Inhibition of restriction endonuclease Nei I cleavage by phosphorothioate groups and its application to oligonucleotide-directed mutagenesis".

Norris et al., 1979, *Gene*, 7(3-4):355-362 "Asymmetric linker molecules for recombinant DNA constructions".

Oefner et al., 1992, *EMBO J.*, 11(11):3921-3926 "Crystal structure of human platelet-derived growth factor BB".

Park et al., 1994, *Journal of Biological Chemistry*, 269(41):25646-25654 "Placenta growth factor. Potentiation of vascular endothelial growth factor bioactivity, in vitro and in vivo, and high affinity binding to Flt-I but not Flk-1/KDR".

Potgens et al., 1994, *Journal of Biological Chemistry*, 269(52):32879-32885 "Covalent dimerization of vascular permeability factor/vascular endothelial growth factor is essential for its biological activity. Evidence from cys to ser mutations".

Sambrook et al., 1989, In *Molecular Cloning: A Laboratory Manual*, Cold Spring Harbor Laboratory Press: Cold Spring Harbor, New York, Part 1:C 5.28-5.32.

Sanger et al., 1977, *Proc. Natl. Acad. Sci. USA*, 74(12):5463-5467 "DNA Sequencing with Chain-terminating Inhibitors".

Schulz et al., 1979, In *Principles of Protein Structure*, Springer Verlag: New York, NY, pp. 14-16.

Sidman et al., 1983, *Biopolymers*, 22(1):547-556 "Controlled Release of Macromolecules and Pharmaceuticals from Synthetic Polypeptides Based on Glutamic Acid".

Siebenlist et al., 1980, *Cell*, 20:269-281 "*E. coli* RNA Polymerase Interacts Homologously with Two Different Promoters".

Southern, E., 1975, *J. Mol. Biol.*, 98:503-517 "Detection of Specific Sequences Among DNA Fragments Separated by Gel Electrophoresis".

Stinchcomb et al., 1979, *Nature*, 282:39-43 "Isolation and Characterization of a Yeast Chromosomal Replicator".

Struck and Lennarz, 1980, In *The Biochemistry of Glycoproteins and Proteoglycons*, W. J. Lennarz Plenum Press, Chapter 2, pp. 35-38 "The Function of Saccharid-Lipids in Synthesis of Glycoproteins".

Tanner and Lehle, *Biochimica et Biophysica Acta*, 906(1):81-99 "Protein glycosylation in yeast".

Taylor et al., 1976, *Biochimica et Biophysica Acta*, 442:324-330 "Efficient Transcription of RNA into DNA by Avian Sarcoma Virus Polymerase".

Tschumper et al., 1980, *Gene*, 10:157-166 "Sequence of a Yeast DNA Fragment Containing a Chromosomal Replicator and the TRP1 Gene".

Ullrich et al., 1977, *Science*, 196:1313-1319 "Rat insulin genes: construction of plasmids containing the coding sequences".

Urlaub et al., 1980, *Proc. Natl. Acad. Sci. USA*, 77(7):4216-4220 "Isolation of Chinese Hamster Cell Mutants Deficient in Dihydrofolate Reductase Activity".

Van Solingen et al., 1977, *J. Bact.*, 130(2):946-947 "Fusion of Yeast Spheroplasts".

Vieira and Messing, 1982, *Gene*, 19(3):259-268 "The pUC plasmids, and M13mp7-derived system for insertion mutagenesis and sequencing with synthetic universal primers".

Vieira et al., 1987, *Methods in Enzymology*, 153:3-11 "Production of Single-stranded Plasmid DNA".

Wartell and Reznikoff, 1980, *Gene*, 9(3-4):307-319 "Cloning DNA restriction endonuclease fragments with protruding single-stranded ends".

Wickens et al., 1978, *Journal of Biological Chemistry*, 253(7):2483-2495 "Synthesis of Double-Stranded DNA Complementary to Lysozyme, Ovomucoid, and Ovalbumin mRNAs".

Winzler, R., 1973, In *Hormonal Proteins and Peptids*, Li, C.I., ed., Academic Press: New York, Chapter 1, pp. 1-15 "The Chemistry of Glycoproteins".

\* cited by examiner

```
  1  CAGTGTGCTG GCGGCCCGGC GCGAGCCGGC CCGGCCCCGG TCGGGCCTCC
-26

GAAACC  ATG AAC TTT CTG CTG TCT TGG GTG CAT TGG AGC
             M   N   F   L   L   S   W   V   H   W   S
             -26                         -20

90  CTC GCC TTG CTG CTC TAC CTC CAC CAT GCC AAG TGG TCC CAG
-15  L   A   L   L   L   Y   L   H   H   A   K   W   S   Q
                             -10

GCT|GCA CCC ATG GCA GAA GGA GGA GGG CAG AAT CAT CAC
     A  |A   P   M   A   E   G   G   G   Q   N   H   H
     -1  +1              +5                      +10

171  GAA GTG GTG AAG TTC ATG GAT GTC TAT CAG CGC AGC TAC TGC
 13  E   V   V   K   F   M   D   V   Y   Q   R   S   Y   C
             +15                 +20                 +25

CAT CCA ATC GAG ACC CTG GTG GAC ATC TTC CAG GAG TAC
     H   P   I   E   T   L   V   D   I   F   Q   E   Y
                 +30                 +35

252  CCT GAT GAG ATC GAG TAC ATC TTC AAG CCA TCC TGT GTG CCC
 40  P   D   E   I   E   Y   I   F   K   P   S   C   V   P
     +40                 +45                 +50

CTG ATG CGA TGC GGG GGC TGC TGC AAT GAC GAG GGC CTG
     L   M   R   C   G   G   C   C   N   D   E   G   L
             +55             +60                 +65

333  GAG TGT GTG CCC ACT GAG GAG TCC AAC ATC ACC ATG CAG ATT
 67  E   C   V   P   T   E   E   S   N   I   T   M   Q   I
                 +70                 +75                 +80

ATG CGG ATC AAA CCT CAC CAA GGC CAG CAC ATA GGA GAG
     M   R   I   K   P   H   Q   G   Q   H   I   G   E
                 +85                 +90

414  ATG AGC TTC CTA CAG CAC AAC AAA TGT GAA TGC AGA CCA AAG
 94  M   S   F   L   Q   H   N   K   C   E   C   R   P   K
         +95                 +100                +105

AAA GAT AGA GCA AGA CAA GAA AAT CCC TGT GGG CCT TGC
     K   D   R   A   R   Q   E   N   P   C   G   P   C
             +110                +115                +120

495  TCA GAG CGG AGA AAG CAT TTG TTT GTA CAA GAT CCG CAG ACG
121  S   E   R   R   K   H   L   F   V   Q   D   P   Q   T
                     +125                +130

TGT AAA TGT TCC TGC AAA AAC ACA GAC TCG CGT TGC AAG
     C   K   C   S   C   K   N   T   D   S   R   C   K
     +135            +140                +145
```

FIG. 1A

```
576  GCG AGG CAG CTT GAG TTA AAC GAA CGT ACT TGC AGA TGT GAC
148   A   R   Q   L   E   L   N   E   R   T   C   R   C   D
             +150                +155                +160

AAG CCG AGG CGG TGA GCCGGGCA GGAGGAAGGA GCCTCCCTCA
      K   P   R   R   O
                 +165

661  GGGTTTCGGG AACCAGATCT CTCACCAGGA AAGACTGATA CAGAACGATC

GATACAGAAA CCACGCTGCC GCCACCACAC CATCACCATC GACAGAACAG

761  TCCTTAATCC AGAAACCTGA AATGAAGGAA GAGGAGACTC TGCGCAGAGC

ACTTGGGTC CGGAGGGCGA GACTCCGGCG GAAGCATTCC CGGGCGGGTG

861  ACCCAGCACG GTCCCTCTTG GAATTGGATT CGCCATTTTA TTTTTCTTGC

TGCTAAATCA CCGAGCCCGG AAGATTAGAG AGTTTTATTT CTGGGATTCC

961  TGTAGACACA CCGCGGCCGC CAGCACACTG
```

FIG. 1B

| Loci | Mutation | Loci | Mutation |
|---|---|---|---|
| 5 | E5A | 64 | E64A |
| 12 | H11A,H12A,E13A | 64.7 | D63A,E64A,E67A |
| 17.5 | K16A,D19T | 67 | E67A |
| 23 | R23A | 72.5 | E72A,E73A |
| 27 | H27A | 82 | R82A |
| 28.5 | H27A,E30A | 84 | K84A |
| 30 | E30A | 84 | R82A,K84A,H86A |
| 34 | D34A | 86 | H86A |
| 36 | D34A,E38A | 91.5 | H90A,E93A |
| 38 | E38A | 100 | H99A,K101A |
| 41 | D41A | 103 | E103A |
| 42 | E42A | 105 | R105A |
| 42.3 | D41A,E42A,E44A | 107.5 | K107A,K108A |
| 44 | E44A | 108.5 | KKDR(107-110)AAAA |
| 48 | K48A | 109.5 | D109A,R110A |
| 56 | R56A | 113 | R112A,E114A |
| 63 | D63A | | |

FIG. 5

VARIANTS OF VASCULAR ENDOTHELIAL CELL GROWTH FACTOR, THEIR USES, AND PROCESSES FOR THEIR PRODUCTION

CROSS-REFERENCE TO RELATED APPLICATIONS

This application is a continuation of U.S. patent application Ser. No. 09/346,069 filed 1 Jul. 1999, now U.S. Pat. No. 7,005,505, which is a continuation of U.S. patent application Ser. No. 08/567,200 filed 5 Dec. 1995, now U.S. Pat. No. 6,020,473, which claims priority to provisional patent application Ser. No. 60/002,827 filed 25 Aug. 1995, the disclosures of which are incorporated in their entirety.

This application contains subject matter related to patent application U.S. Ser. No. 389,722, filed 4 Aug. 1989 now U.S. Pat. No. 5,332,671 and to its parent applications, U.S. Ser. No. 369,424 filed 21 Jun. 1989 and U.S. Ser. No. 351,117 filed 12 May 1989.

FIELD OF THE INVENTION

The present invention is directed to particular variants of vascular endothelial cell growth factor (hereinafter sometimes referred to as VEGF), to methods for preparing such variants, and to methods and compositions and assays utilizing such variants for producing pharmaceutically active materials having therapeutic and pharmacologic properties that differ from the parent compound, VEGF. In particular, the assays using such variants can be employed to discover new materials having agonistic or antagonistic properties to VEGF.

BACKGROUND OF THE INVENTION

VEGF is a naturally occurring compound that is produced in follicular or folliculo-stellate cells (FC), a morphologically well characterized population of granular cells. The FC are stellate cells that send cytoplasmic processes between secretory cells.

Several years ago a heparin-binding endothelial cell-growth factor called vascular endothelial growth factor (VEGF) was identified and purified from media conditioned by bovine pituitary follicular or folliculo-stellate cells. See Ferrara et al., *Biophys. Res. Comm.* 161, 851 (1989).

Although a vascular endothelial cell growth factor could be isolated and purified from natural sources for subsequent therapeutic use, the relatively low concentrations of the protein in FC and the high cost, both in terms of effort and expense, of recovering VEGF proved commercially unavailing. Accordingly, further efforts were undertaken to clone and express VEGF via recombinant DNA techniques. The embodiments of that research are set forth in the patent applications referred to supra; this research was also reported in the scientific literature in *Laboratory Investigation* 72, 615 (1995), and the references cited therein.

In those applications there is described an isolated nucleic acid sequence comprising a sequence that encodes a vascular endothelial cell growth factor having a molecular weight of about 45,000 daltons under non-reducing conditions and about 23,000 under reducing conditions as measured by SDS-PAGE. Both the DNA and amino acid sequences are set forth in figures forming a part of the present application—see infra.

VEGF prepared as described in the patent applications cited supra, is useful for treating conditions in which a selected action on the vascular endothelial cells, in the absence of excessive tissue growth, is important, for example, diabetic ulcers and vascular injuries resulting from trauma such as subcutaneous wounds. Being a vascular (artery and venus) endothelial cell growth factor, VEGF restores cells that are damaged, a process referred to as vasculogenesis, and stimulates the formulation of new vessels, a process referred to as angiogenesis.

VEGF is expressed in a variety of tissues as multiple homodimeric forms (121, 165, 189 and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release (a) diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (4.6.1 and 2E3) and soluble forms of FLT-1, KDR and FLK receptors with similar affinity compared to the intact $VEGF_{165}$ homodimer.

As noted, VEGF contains two domains that are responsible respectively for binding to the KDR (kinase domain region) and FLT-1 (FMS-like tyrosine kinase) receptors. These receptors exist only on endothelial (vascular) cells. As cells become depleted in oxygen, because of trauma and the like, VEGF production increases in such cells which then bind to the respective receptors in order to signal ultimate biological effect. The signal then increases vascular permeability and the cells divide and expand to form new vascular pathways-vasculogenesis and angiogenesis. Thus, VEGF and derivatives thereof, as described in the patent applications referred to supra, would find use in the restoration of vasculature after a myocardial infarct, as well as other uses that can be deduced.

The present invention is predicated upon research intended to identify the regions or domains that are responsible for binding to the KDR and FLT receptors. After identification, it was a goal to mutagenize such a domain in order to produce variants that have either increased or decreased binding capability with respect to those respective KDR and FLT binding domains.

It was a further object of this research to produce VEGF variants that would have selective activity with respect to the binding KDR and FLT domains. It was postulated that if one could increase the binding capability of the domain responsible for vasculogenesis and angiogenesis, one could produce a more potent material for intended therapeutic use. Conversely, if one could by induced mutagenesis produce VEGF variants that had reduced activity, and consequently, anti-vasculogenesis and anti-angiogenesis, one could use such variants in instances of tumor treatment in order to starve the tumors for intended regression.

As further objects, such variants could then be employed in assay systems to discover small molecule agonists and antagonists for intended therapeutic use in such indications.

The results of such research is the subject of the present invention. The dominant domains of VEGF for receptor binding were found to be proximately located, but at distinct sites, allowing the development of variants that proved to be receptor-selective. The KDR receptor was found to bind VEGF predominantly through the sites on a putative loop which contains Arginine (Arg or R) at position 82 of VEGF, Lysine (Lys or K) at position 84 and Histidine (His or H) at position 86. The FLT-1 receptor was found to bind VEGF predominantly through the sites on a putative loop which contains Aspartic acid (Asp or D) at position 63, Glutamic acid (Glu or E) at position 64 and Glutamic acid (Glu or B) at position 67.

Mutagenesis experiments followed with respect generally to these domains resulting in the variants of the present invention. Such mutagenesis employed both specific and random strategies, in accordance with procedures generally well known to the art-skilled.

SUMMARY OF THE INVENTION

The objects of this invention, as defined generally supra, are achieved by the provision of a vascular endothelial cell growth factor (VEGF) variant having mutations in the Kinase domain region (KDR) and/or the FMS-like Tyrosine-Kinase region (FLT-1), said variants exhibiting modified binding characteristics at said regions compared with native VEGF.

In a preferred embodiment, such mutagenesis is effected within the region bounded by amino acids within the approximate positions 78 to 95 of VEGF.

In another embodiment, such mutagenesis is effected within the region bounded by amino acids within the approximate positions 60 to 70 of VEGF.

In another embodiment such mutagenesis is effected at both said regions.

In a particularly preferred embodiment, mutagenesis is effected at least at positions 82, 84 and 86 of VEGF and/or positions 63, 64 and 67 of VEGF.

In still another particularly preferred embodiment, VEGF variants are produced in which mutagenesis is created at positions 82, 84 and 86 as follows: R82A, K84A and H86A and/or D63A, E64A and E67A. These symbols signify the change made at the respective positions, for example, the Arginine (R) codon at position 82 was mutated to produce an Alanine (A) at that position, etc.

In other embodiments, the present invention relates to DNA sequences encoding the various variants described supra, replicable expression vectors capable of expressing said DNA sequences via transforming DNA in a transformant host cell, and microorganisms and cell cultures which are transformed with such vectors.

In yet further embodiments, the present invention is directed to compositions useful for treating indications where vasculogenesis or angiogenesis is desired for treatment of the underlying disease state comprising a therapeutically effective amount of a VEGF variant hereof in admixture with a pharmaceutically acceptable carrier.

In still another embodiments the present invention is directed to a composition for treating indications where antivascular-genesis or antiangio-genesis is desired, such as in arresting tumors, comprising a therapeutically effective amount of a variant hereof in admixture with a pharmaceutically acceptable carrier.

In particular, mutations in accordance with the present invention that have been introduced generally at positions spanning the region of amino acids 78 to 95, and more particularly 82 to 86, create variants that bind normally to the FLT receptor but have significantly reduced binding properties with respect to the KDR receptor. Mutations in accordance with the present invention that have been introduced generally at positions spanning the region of amino acids 60 to 70, and more particularly 63 to 67, create variants that bind essentially normally to the KDR receptor but have significantly reduced binding with respect to the FLT receptor.

Expanding on the basic premise hereof of the discovery and mutagenesis of the KDR and/or FLT binding domains of VEGF, the present invention is directed to all associated embodiments deriving therefrom, including recombinant DNA materials and processes for preparing such variants, materials and information for compounding such variants into pharmaceutically finished form and assays using such variants to screen for candidates that have agonistic or antagonistic properties with respect to the KDR and/or FLT receptors.

BRIEF DESCRIPTION OF THE DRAWINGS

FIG. 1 depicts both the amino acid (SEQ ID NO: 2) and DNA sequence (SEQ ID NO:1) for VEGF having 165 amino acids. Predicted amino acids of the protein are shown below the DNA sequence and are numbered from the first residue of the N-terminus of the protein sequence. Negative amino acid numbers refer to the presumed leader signal sequence or pre-protein, while positive numbers refer to the putative mature protein.

FIG. 5 shows the charged-to-Alanine scan mutations hereof in VEGF.

Figure 20:
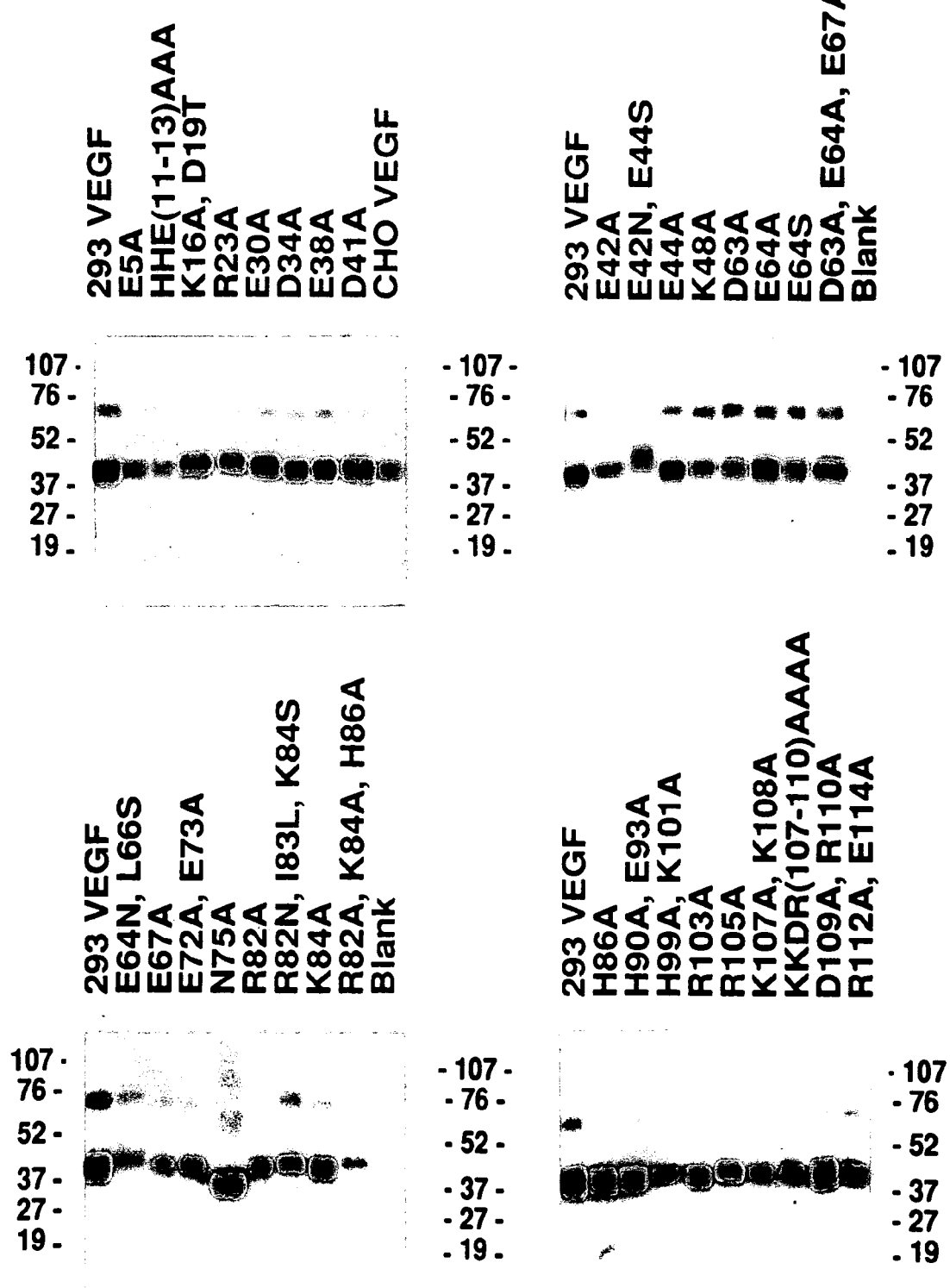

FIG. 20 shows the SDS-PAGE Immunoblot of VEGF mutants. Transient transfection supernatants (from 293 cells) containing approximately 10 to 20 ng of VEGF or VEGF mutant were analyzed by non-reduced SDS-PAGE. The gels were transferred and blotted as described in the Experimental Procedures, using a panel of 5 murine monoclonal antihuman VEGF$_{165}$ antibodies identified as the following: 2E3, 4D7, A4.6.1, 5C3, and 5F8. The immunoblots were exposed for 5 days.

Figure 21:
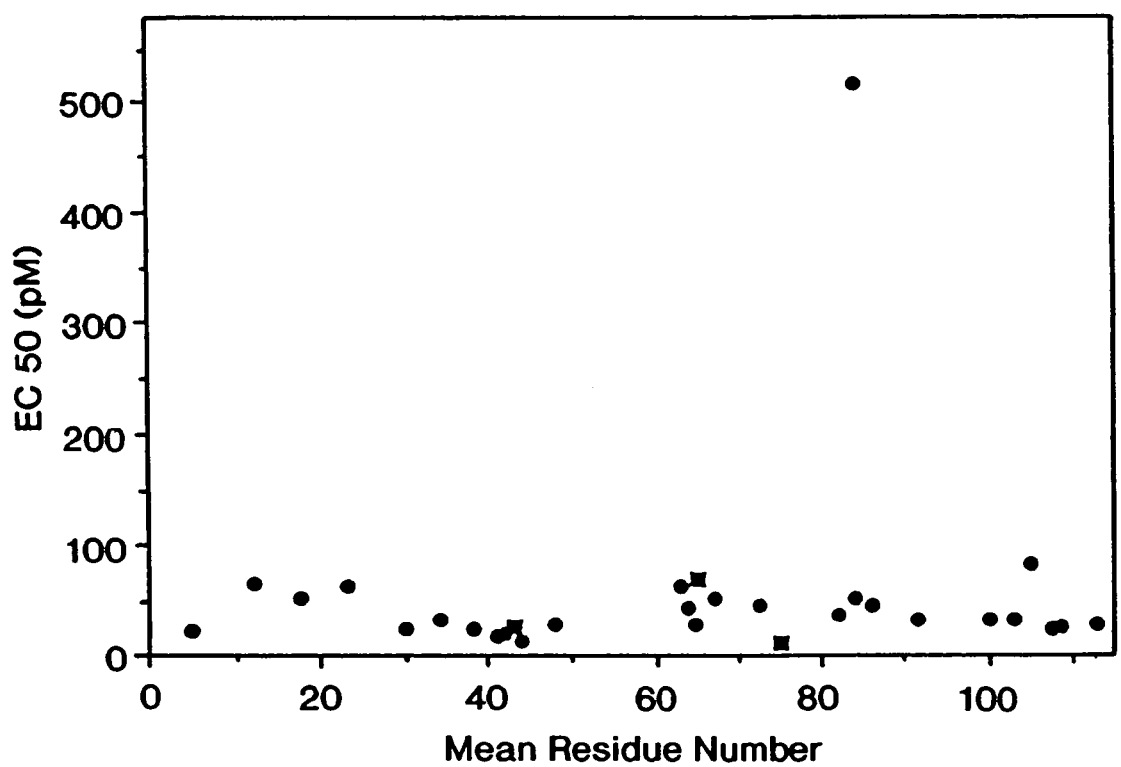

FIG. 21 shows activity of VEGF mutants in endothelial cell growth assay. The VEGF mutants were expressed in 293 cell culture, the conditioned cell media was used to stimulate mitogenesis of bovine adrenal cortical capillary endothelial cells. The mean residue number indicates the location of the mutations. The values are expressed as the concentration required to half-maximally stimulate endothelial cell proliferation ($EC_{50}$). Alanine mutants of VEGF are indicated as filled circles and potential extra-glycosylated VEGF mutants are filled boxes. These experiments were done in triplicate.

DETAILED DESCRIPTION OF THE INVENTION

A. Definitions

As used herein, "vascular endothelial cell growth factor," or "VEGF," refers to a mammalian growth factor as defined in U.S. Pat. No. 5,332,671, including the human amino acid sequence of FIG. 1 (SEQ ID NOs: 1 and 2). The biological activity of native VEGF is shared by any analogue or variant thereof that is capable of promoting selective growth of vascular endothelial cells but not of bovine corneal endothelial cells, lens epithelial cells, adrenal cortex cells, BHK-21 fibroblasts, or keratinocytes, or that possesses an immune epitope that is immunologically cross-reactive with an antibody raised against at least one epitope of the corresponding native VEGF.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (*USA*), 69, 2110 (1972) and Mandel et al. *J. Mol. Biol.* 53, 154 (1970), is generally used for prokaryotes or other cells that contain substantial cell-wall barriers. For mammalian cells without such cell walls, the calcium phosphate precipitation method of Graham, F. and van der Eb, A., *Virology*, 52, 456-457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. *J. Bact.*, 130, 946 (1977) and Hsiao, C. L., et al. *Proc. Natl. Acad. Sci.* (*USA*) 76, 3829 (1979). However, other methods for introducing DNA into cells such as by nuclear injection or by protoplast fusion may also be used.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do not exist, then synthetic oligonucleotide adaptors or linkers are used in accord with conventional practice.

"Control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 mg of plasmid or DNA fragment is used with about 1-2 units of enzyme in about 20 ml of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al. 1982, *Molecular Cloning: A Laboratory Manual* (New York: Cold Spring Harbor Laboratory, 1982) pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9, 6103-6114 (1981), and D. Goeddel et al., *Nucleic Acids Res.* 8, 4057 (1980).

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation, and transfer to nitrocellulose by the method of E. Southern, *J. Mol. Biol.* 98, 503-517 (1975), and hybridization as described by T. Maniatis et al., *Cell* 15, 687-701 (1978).

"Ligation" refers to the process of forming phosphodiester bonds between two double stranded nucleic acid fragments (T. Maniatis et al. 1982, supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.* 14, 5399-5407 [1986]). They are then purified on polyacrylamide gels.

The abbreviation "KDR" refers to the kinase domain region of the VEGF molecule. It is this region which is known to bind to the kinase domain region receptor.

The abbreviation "FLT-1" refers to the FMS-like tyrosine kinase binding domain which is known to bind to the corresponding FLT-1 receptor. These receptors exist on the surfaces of endothelial cells.

B. General Methodology

1. Glycosylation

The VEGF amino acid sequence variant may contain at least one amino acid sequence that has the potential to be glycosylated through an N-linkage and that is not normally glycosylated in the native molecule.

Introduction of an N-linked glycosylation site in the variant requires a tripeptidyl sequence of the formula: asparagine-X-serine or asparagine-X-threonine, wherein asparagine is the acceptor and X is any of the twenty genetically encoded amino acids except proline, which prevents glycosylation. See D. K. Struck and W. J. Lennarz, in *The Biochemistry of Glycoproteins and Proteoglycans*, ed. W. J. Lennarz, Plenum Press, 1980, p. 35; R. D. Marshall, *Biochem. Soc. Symp.*, 40, 17 (1974), and Winzler, R. J., in *Hormonal Proteins and Peptides* (ed. Li, C.I.) p. 1-15 (Academic Press, New York, 1973). The amino acid sequence variant herein is modified by substituting for the amino acid(s) at the appropriate site(s) the appropriate amino acids to effect glycosylation.

If O-linked glycosylation is to be employed, O-glycosidic linkage occurs in animal cells between N-acetylgalactosamine, galactose, or xylose and one of several hydroxyamino acids, most commonly serine or threonine, but also in some cases a 5-hydroxyproline or 5-hydroxylysine residue placed in the appropriate region of the molecule.

Glycosylation patterns for proteins produced by mammals are described in detail in *The Plasma Proteins: Structure, Function and Genetic Control*, F. W. Putnam, ed., 2nd edition, volume 4 (Academic Press, New York, 1984), p. 271-315, the entire disclosure of which is incorporated herein by reference. In this chapter, asparagine-linked oligosaccharides are discussed, including their subdivision into at least three groups referred to as complex, high mannose, and hybrid structures, as well as O-glucosidically linked oligosaccharides.

Chemical and/or enzymatic coupling of glycosides to proteins can be accomplished using a variety of activated groups, for example, as described by Aplin and Wriston in *CRC Crit. Rev. Biochem.*, pp. 259-306 (1981), the disclosure of which is incorporated herein by reference. The advantages of the chemical coupling techniques are that they are relatively simple and do not need the complicated enzymatic machinery required for natural O- and N-linked glycosylation. Depending on the coupling mode used, the sugar(s) may be attached to (a) arginine or histidine, (b) free carboxyl groups such as those of glutamic acid or aspartic acid, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described more fully in PCT WO 87/05330 published Sep. 11, 1987, the disclosure of which is incorporated herein by reference.

Glycosylation patterns for proteins produced by yeast are described in detail by Tanner and Lehle, *Biochim. Biophys. Acta*, 906(1), 81-99 (1987) and by Kukuruzinska et al., *Annu. Rev. Biochem.*, 56, 915-944 (1987), the disclosures of which are incorporated herein by reference.

2. Amino Acid Sequence Variants a. Additional Mutations

For purposes of shorthand designation of VEGF variants described herein, it is noted that numbers refer to the amino acid residue/position along the amino acid sequences of putative mature VEGF. Amino acid identification uses the single-letter alphabet of amino acids, i.e.,

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptophan |
| Val | V | Valine | Gln | Q | Glutamine |
| Met | M | Methionine | Asn | N | Asparagine |

The present invention is directed to variants of VEGF where such variants have modifications in the amino acid sequence in two of the receptor binding domains: 1) from within the range of amino acid of about 78 to 95 and 2) in the range of amino acid at position about 60 to 70. These variants have selective activity with respect to the respective binding sites of the corresponding receptors.

It will be appreciated that certain other variants at other positions in the VEGF molecule can be made without departing from the spirit of the present invention with respect to the two receptor binding site variations. Thus point mutational or other broader variations may be made in all other parts of the molecule so as to impart interesting properties that do not effect the overall properties of the variants with respect to the domains from 78 to 95 and 60 to 70.

These latter, additional variants may be made by means generally known well in the art.

For example covalent modifications may be made to various of the amino acid residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-b-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N—C—N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Derivatization with bifunctional agents is useful for crosslinking the VEGF to a water-insoluble support matrix or surface for use in the method for purifying anti-VEGF antibodies. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, Proteins: Structure and Molecular Properties, W.H. Freeman & Co., San Francisco, pp. 79-86 [1983]), acetylation of the N-terminal amine, and, in some instances, amidation of the C-terminal carboxyl group.

b. DNA Mutations

Amino acid sequence variants of VEGF can also be prepared by mutations in the DNA. Such variants include, for example, deletions from, or insertions or substitutions of, residues within the amino acid sequence shown in FIG. 1 (SEQ ID NOs: 1 and 2). Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the VEGF, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed VEGF variants screened for the optimal combination of desired activity. Techniques for making substitution mutations at predetermined sites in DNA having a known sequence are well known, for example, site-specific mutagenesis.

Preparation of VEGF variants in accordance herewith is preferably achieved by site-specific mutagenesis of DNA that encodes an earlier prepared variant or a nonvariant version of the protein. Site-specific mutagenesis allows the production of VEGF variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA* 2, 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well known to those skilled in the art. Alternatively, plasmid vectors that contain a single-stranded phage origin of replication (Veira et al., *Meth. Enzymol.,* 153, 3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (*USA*), 75, 5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature VEGF sequence) may range generally from about 1 to 10 residues, more preferably 1 to 5. An example of a terminal insertion includes a fusion of a signal sequence, whether heterologous or homologous to the host cell, to the N-terminus of the VEGF molecule to facilitate the secretion of mature VEGF from recombinant hosts.

The third group of variants are those in which at least one amino acid residue in the VEGF molecule, and preferably only one, has been removed and a different residue inserted in its place. Such substitutions preferably are made in accordance with the following Table 1 when it is desired to modulate finely the characteristics of a VEGF molecule.

TABLE 1

| Original Residue | Exemplary Substitutions |
|---|---|
| Ala (A) | gly; ser |
| Arg (R) | lys |
| Asn (N) | gln; his |
| Asp (D) | glu |
| Cys (C) | ser |
| Gln (Q) | asn |
| Glu (E) | asp |
| Gly (G) | ala; pro |
| His (H) | asn; gln |
| Ile (I) | leu; val |
| Leu (L) | ile; val |
| Lys (K) | arg; gln; glu |
| Met (M) | leu; tyr; ile |
| Phe (F) | met; leu; tyr |
| Ser (S) | thr |
| Thr (T) | ser |
| Trp (W) | tyr |
| Tyr (Y) | trp; phe |
| Val (V) | ile; leu |

Substantial changes in function or immunological identity are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in VEGF properties will be those in which (a) glycine and/or proline (P) is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; (e) a residue having an electronegative side chain is substituted for (or by) a residue having an electropositive charge; or (f) a residue having a bulky side chain, e.g., phenylalanine, is substituted for (or by) one not having such a side chain, e.g., glycine.

Most deletions and insertions, and substitutions in particular, are not expected to produce radical changes in the characteristics of the VEGF molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native VEGF-encoding nucleic acid, expression of the variant nucleic acid in recombinant cell culture, and, optionally, purification from the cell culture, for example, by immunoaffinity adsorption on a rabbit polyclonal anti-VEGF column (to absorb the variant by binding it to at least one remaining immune epitope).

Since VEGF tends to aggregate into dimers, it is within the scope hereof to provide hetero- and homodimers, wherein one or both subunits are variants. Where both subunits are variants, the changes in amino acid sequence can be the same or different for each subunit chain. Heterodimers are readily produced by cotransforming host cells with DNA encoding both subunits and, if necessary, purifying the desired heterodimer, or by separately synthesizing the subunits, dissociating the subunits (e.g., by treatment with a chaotropic agent such as urea, guanidine hydrochloride, or the like), mixing the dissociated subunits, and then reassociating the subunits by dialyzing away the chaotropic agent.

Also included within the scope of mutants herein are so-called glyco-scan mutants. This embodiment takes advantage of the knowledge of so-called glycosylation sites which are identified by the sequence—$NXS_T$ wherein N represents the amino acid asparagine, X represents any amino acid except proline and probably glysine and the third position can be occupied by either amino acid serine or threonine. Thus, where appropriate such a glycosylation site can be introduced so as to produce a species containing glycosylation moieties at that position. Similarly, an existing glycosylation site can be removed by mutation so as to produce a species that is devoid of glycosylation at that site. It will be understood, again, as with the other mutations contemplated by the present invention, that they are introduced within the so-called KDR and/or FLT-1 domains in accord with the basic premise of the present invention, and they can be introduced at other locations outside of these domains within the overall molecule so long as the final product does not differ in overall kind from the properties of the mutation introduced in one or both of said two binding domains.

The activity of the cell lysate or purified VEGF variant is then screened in a suitable screening assay for the desired characteristic. For example, a change in the immunological character of the VEGF molecule, such as affinity for a given antibody, is measured by a competitive-type immunoassay. Changes in the enhancement or suppression of vascular endothelium growth by the candidate mutants are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

3. Recombinant Expression

The VEGF molecule desired may be prepared by any technique, including recombinant methods. Likewise, an isolated DNA is understood herein to mean chemically synthesized DNA, cDNA, chromosomal, or extrachromosomal DNA with or without the 3'- and/or 5'-flanking regions. Preferably, the desired VEGF herein is made by synthesis in recombinant cell culture.

Figure 2:
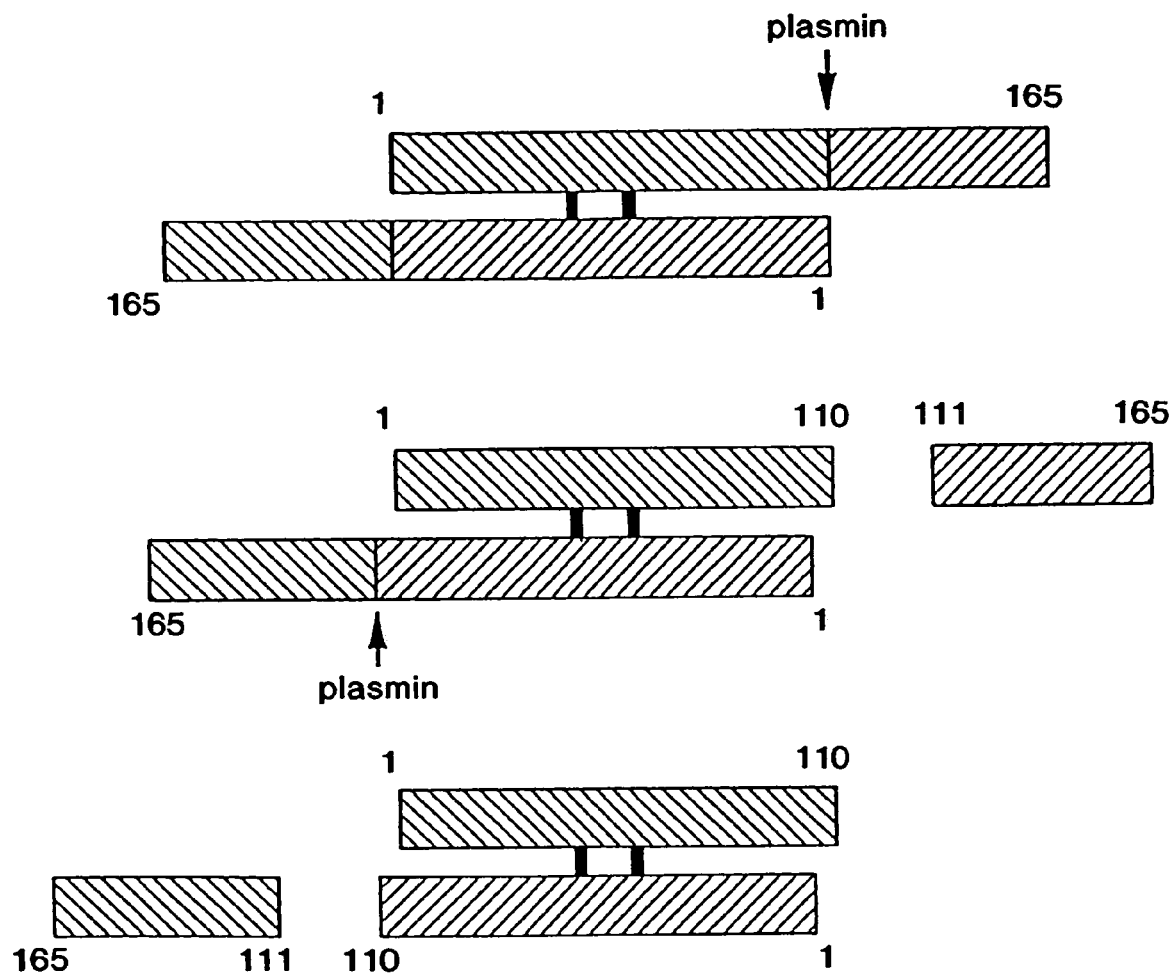
FIG. 2 depicts the various domains of $VEGF_{165}$ and shows the plasmin cleavage site. The receptor binding domains are located within the region spanning amino acids 1 to 110.
Figure 3:
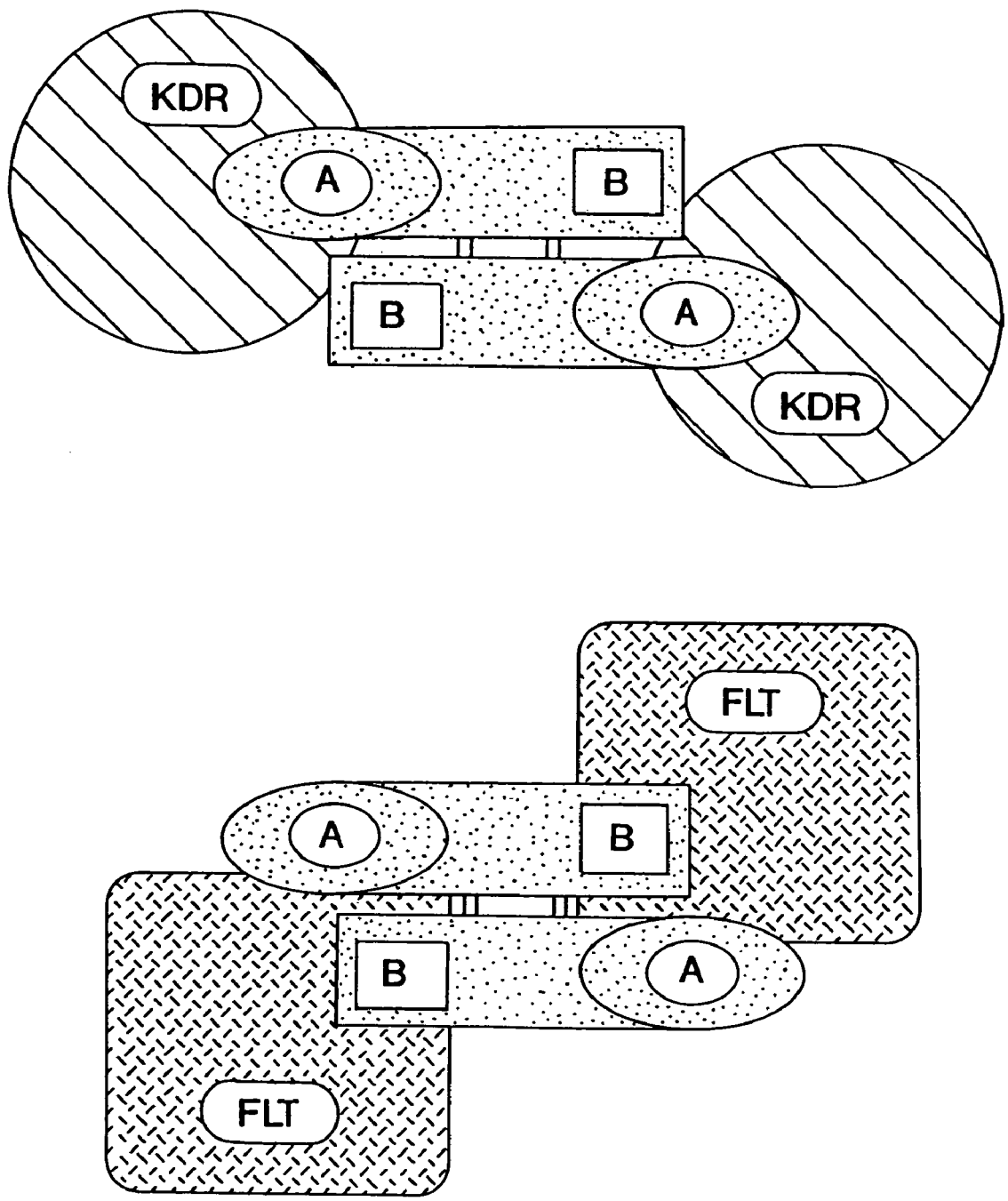
FIG. 3 displays the separate and distinct receptor binding sites for the KDR and FLT receptors. These sites are located respectively in the region spanning generally amino acids 78 to 90 (depicted as "A" in FIG. 3) and 60 to 70 (depicted as "B").
Figure 10:
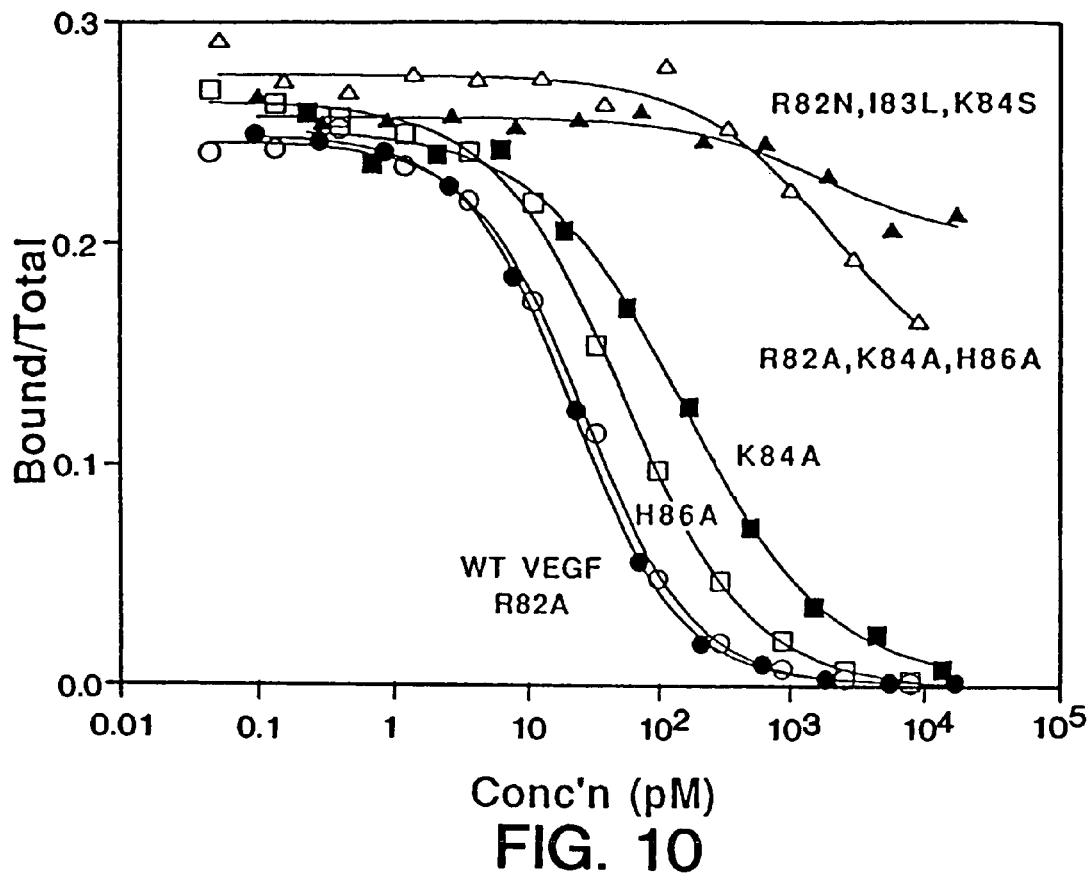
FIG. 10 shows that multiple mutations have a synergistic effect with KDR: K84A is a potent single Alanine substitution.

For such synthesis, it is first necessary to secure nucleic acid that encodes a VEGF. DNA encoding a VEGF molecule may be obtained from bovine pituitary follicular cells by (a) preparing a cDNA library from these cells, (b) conducting hybridization analysis with labeled DNA encoding the VEGF or fragments thereof (up to or more than 100 base pairs in length) to detect clones in the library containing homologous sequences, and (c) analyzing the clones by restriction enzyme analysis and nucleic acid sequencing to identify full-length clones. DNA that is capable of hybridizing to a VEGF-encoding DNA under low stringency conditions is useful for identifying DNA encoding VEGF. Both high and low stringency conditions are defined further below. If full-length clones are not present in a cDNA library, then appropriate fragments may be recovered from the various clones using the nucleic acid sequence information disclosed herein for the first time and ligated at restriction sites common to the clones to assemble a full-length clone encoding the VEGF. Alternatively, genomic libraries will provide the desired DNA. The sequence of the DNA encoding bovine VEGF that was ultimately determined is shown in FIG. 2. The sequence of the DNA encoding human VEGF that was ultimately determined by probing a human leukemia cell line is shown in FIG. 10.

Once this DNA has been identified and isolated from the library it is ligated into a replicable vector for further cloning or for expression.

In one example of a recombinant expression system a VEGF-encoding gene is expressed in mammalian cells by transformation with an expression vector comprising DNA encoding the VEGF. It is preferable to transform host cells capable of accomplishing such processing so as to obtain the VEGF in the culture medium or periplasm of the host cell, i.e., obtain a secreted molecule.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., *Gene* 2, 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the b-lactamase (penicillinase) and lactose promoter systems (Chang et al., *Nature*, 375,615 [1978]; Itakura et al., *Science,* 198, 1056 [1977]; Goeddel et al., *Nature,* 281, 544 [1979]) and a tryptophan (trp) promoter system (Goeddel et al., *Nucleic Acids Res.,* 8, 4057 [1980]; EPO Appl. Publ. No. 0036,776). While these are the most commonly used, other microbial promoters have been discovered and utilized, and details concerning their nucleotide sequences have been published, enabling a skilled worker to ligate them functionally with plasmid vectors (see, e.g., Siebenlist et al., *Cell,* 20, 269 [1980]).

In addition to prokaryotes, eukaryotic microbes, such as yeast cultures, may also be used. *Saccharomyces cerevisiae,* or common baker's yeast, is the most commonly used among eukaryotic microorganisms, although a number of other strains are commonly available. For expression in *Saccharomyces,* the plasmid YRp7, for example (Stinchcomb et al., *Nature* 282, 39 [1979]; Kingsman et al., *Gene* 7, 141 [1979]; Tschemper et al., *Gene* 10, 157 [1980]), is commonly used. This plasmid already contains the trp1 gene that provides a selection marker for a mutant strain of yeast lacking the ability to grow in tryptophan, for example, ATCC No. 44,076 or PEP4-1 (Jones, *Genetics,* 85, 12 [1977]). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 [1980]) or other glycolytic enzymes (Hess et al., *J. Adv. Enzyme Reg.* 7, 149 [1968]; Holland et al., *Biochemistry* 17, 4900 [1978]), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture,* Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication [Fiers et al., *Nature,* 273, 113 (1978)]. Smaller or larger SV40 fragments may also be used, provided there is included the approximately 250-bp sequence extending from the HindIII site toward the BgII site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by an externally controlled parameter, such as methotrexate (MTX), thus permitting control of expression by control of the methotrexate concentration.

In selecting a preferred host cell for transfection by the vectors of the invention that comprise DNA sequences encoding both VEGF and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (*USA*) 77, 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.* 8, 4057 (1980).

For analysis to confirm correct sequences in plasmids constructed, the ligation mixtures are typically used to transform *E. coli* K 12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.* 9, 309 (1981) or by the method of Maxam et al., *Methods of Enzymology* 65, 499 (1980).

After introduction of the DNA into the mammalian cell host and selection in medium for stable transfectants, amplification of DHFR-protein-coding sequences is effected by growing host cell cultures in the presence of approximately 20,000-500,000 nM concentrations of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in a section just prior to the examples.

4. Utilities and Formulation

The VEGF molecules herein have a number of therapeutic uses associated with the vascular endothelium. Such uses include the treatment of traumata to the vascular network, in view of the demonstrated rapid promotion by VEGF of the proliferation of vascular endothelial cells that would surround the traumata. Examples of such traumata that could be so treated include, but are not limited to, surgical incisions, particularly those involving the heart, wounds, including lacerations, incisions, and penetrations of blood vessels, and surface ulcers involving the vascular endothelium such as diabetic, haemophiliac, and varicose ulcers. Other physiological conditions that could be improved based on the selective mitogenic character of VEGF are also included herein.

For the traumatic indications referred to above, the VEGF molecule will be formulated and dosed in a fashion consistent with good medical practice taking into account the specific disorder to be treated, the condition of the individual patient, the site of delivery of the VEGF, the method of administration, and other factors known to practitioners. Thus, for purposes herein, the "therapeutically effective amount" of the VEGF is an amount that is effective either to prevent, lessen the worsening of, alleviate, or cure the treated condition, in particular that amount which is sufficient to enhance the growth of vascular endothelium in vivo.

VEGF amino acid sequence variants and derivatives that are immunologically crossreactive with antibodies raised against native VEGF are useful in immunoassays for VEGF as standards, or, when labeled, as competitive reagents.

The VEGF is prepared for storage or administration by mixing VEGF having the desired degree of purity with physiologically acceptable carriers, excipients, or stabilizers. Such materials are non-toxic to recipients at the dosages and concentrations employed. If the VEGF is water soluble, it may be formulated in a buffer such as phosphate or other organic acid salt preferably at a pH of about 7 to 8. If a VEGF variant is only partially soluble in water, it may be prepared as a microemulsion by formulating it with a nonionic surfactant such as Tween, Pluronics, or PEG, e.g., Tween 80, in an amount of 0.04-0.05% (w/v), to increase its solubility.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

The VEGF to be used for therapeutic administration must be sterile. Sterility is readily accomplished by filtration through sterile filtration membranes (e.g., 0.2 micron membranes). The VEGF ordinarily will be stored in lyophilized form or as an aqueous solution if it is highly stable to thermal and oxidative denaturation. The pH of the VEGF preparations typically will be about from 6 to 8, although higher or lower pH values may also be appropriate in certain instances. It will be understood that use of certain of the foregoing excipients, carriers, or stabilizers will result in the formation of salts of the VEGF.

If the VEGF is to be used parenterally, therapeutic compositions containing the VEGF generally are placed into a container having a sterile access port, for example, an intravenous solution bag or vial having a stopper pierceable by a hypodermic injection needle.

Generally, where the disorder permits, one should formulate and dose the VEGF for site-specific delivery. This is convenient in the case of wounds and ulcers. Sustained release formulations may also be prepared, and include the formation of microcapsular particles and implantable articles. For preparing sustained-release VEGF compositions, the VEGF is preferably incorporated into a biodegradable matrix or microcapsule. A suitable material for this purpose is a polylactide, although other polymers of poly-(a-hydroxycarboxylic acids), such as poly-D-(−)-3-hydroxybutyric acid (EP 133,988A), can be used. Other biodegradable polymers include poly(lactones), poly(acetals), poly(orthoesters), or poly(orthocarbonates). The initial consideration here must be that the carrier itself, or its degradation products, is nontoxic in the target tissue and will not further aggravate the condition. This can be determined by routine screening in animal models of the target disorder or, if such models are unavailable, in normal animals. Numerous scientific publications document such animal models.

For examples of sustained release compositions, see U.S. Pat. No. 3,773,919, EP 58,481A, U.S. Pat. No. 3,887,699, EP 158,277A, Canadian Patent No. 1176565, U. Sidman et al., *Biopolymers* 22, 547 [1983], and R. Langer et al., *Chem. Tech.* 12, 98 [1982].

When applied topically, the VEGF is suitably combined with other ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, the VEGF formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the VEGF held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and the VEGF is present in an amount of about 300-1000 mg per ml of gel.

The dosage to be employed is dependent upon the factors described above. As a general proposition, the VEGF is formulated and delivered to the target site or tissue at a dosage capable of establishing in the tissue a VEGF level greater than about 0.1 ng/cc up to a maximum dose that is efficacious but not unduly toxic. This intra-tissue concentration should be maintained if possible by continuous infusion, sustained release, topical application, or injection at empirically determined frequencies.

It is within the scope hereof to combine the VEGF therapy with other novel or conventional therapies (e.g., growth factors such as aFGF, bFGF, PDGF, IGF, NGF, anabolic steroids, EGF or TGF-a) for enhancing the activity of any of the growth factors, including VEGF, in promoting cell proliferation and repair. It is not necessary that such cotreatment drugs be included per se in the compositions of this invention, although this will be convenient where such drugs are proteinaceous. Such admixtures are suitably administered in the same manner and for the same purposes as the VEGF used alone. The useful molar ratio of VEGF to such secondary growth factors is typically 1:0.1-10, with about equimolar amounts being preferred.

5. Pharmaceutical Compositions

The compounds of the present invention can be formulated according to known methods to prepare pharmaceutically useful compositions, whereby the VEGF variants hereof is combined in admixture with a pharmaceutically acceptable carrier vehicle. Suitable carrier vehicles and their formulation, inclusive of other human proteins, e.g., human serum albumin, are described, for example, in *Remington's Pharmaceutical Sciences,* 16th ed., 1980, Mack Publishing Co., edited by Oslo et al. the disclosure of which is hereby incorporated by reference. The VEGF variants herein may be administered parenterally to subjects suffering from cardiovascular diseases or conditions, or by other methods that ensure its delivery to the bloodstream in an effective form.

Compositions particularly well suited for the clinical administration of VEGF variants hereof employed in the practice of the present invention include, for example, sterile aqueous solutions, or sterile hydratable powders such as lyophilized protein. It is generally desirable to include further in the formulation an appropriate amount of a pharmaceutically acceptable salt, generally in an amount sufficient to render the formulation isotonic. A pH regulator such as arginine base, and phosphoric acid, are also typically included in sufficient quantities to maintain an appropriate pH, generally from 5.5 to 7.5. Moreover, for improvement of shelf-life or stability of aqueous formulations, it may also be desirable to include further agents such as glycerol. In this manner, variant t-PA formulations are rendered appropriate for parenteral administration, and, in particular, intravenous administration.

Dosages and desired drug concentrations of pharmaceutical compositions of the present invention may vary depending on the particular use envisioned. For example, in the treatment of deep vein thrombosis or peripheral vascular disease, "bolus" doses, will typically be preferred with subsequent administrations being given to maintain an approximately constant blood level, preferably on the order of about 3 µg/ml.

However, for use in connection with emergency medical care facilities where infusion capability is generally not available and due to the generally critical nature of the underlying disease (e.g., embolism, infarct), it will generally be desirable to provide somewhat larger initial doses, such as an intravenous bolus.

For the various therapeutic indications referred to for the compounds hereof, the VEGF molecules will be formulated and dosed in a fashion consistent with good medical practice taking into account the specific disorder to be treated, the condition of the individual patient, the site of delivery, the method of administration and other factors known to practitioners in the respective art. Thus, for purposes herein, the "therapeutically effective amount" of the VEGF molecules hereof is an amount that is effective either to prevent, lessen the worsening of, alleviate, or cure the treated condition, in particular that amount which is sufficient to enhance the growth of vascular endothelium in vivo. In general a dosage is employed capable of establishing in the tissue that is the target for the therapeutic indication being treated a level of a VEGF mutant hereof greater than about 0.1 ng/cm$^3$ up to a maximum dose that is efficacious but not unduly toxic. It is contemplated that intra-tissue administration may be the choice for certain of the therapeutic indications for the compounds hereof.

The following examples are intended merely to illustrate the best mode now known for practicing the invention but the invention is not to be considered as limited to the details of such examples.

EXAMPLE 1

Materials—Muta-gene phagemid in vitro mutagenesis kit, horse-radish peroxidase conjugated goat IgG specific for murine IgG, pre-stained low-range MW standards and Trans-Blot Transfer Medium (pure nitrocellulose membrane) were purchased from BioRad Laboratories (Richmond, Calif.). Qiagen plasmid Tip 100 kit and Sequenase version 2.0 were from Qiagen (Chatsworth, Calif.) and United States Biochemical (Cleveland, Ohio), respectively. SDS gels (4-20% gradient polyacrylamide) and pre-cut blotting paper were from Integrated Separations Systems (Natick, Mass.). SDS sample buffer (5× concentrate) and various restriction enzymes were from New England Biolabs (Beverly, Mass.). O-phenylenediamine, citrate phosphate buffers, sodium dodecyl sulfate, and $H_2O_2$ substrate tablets were purchased from Sigma (St. Louis, Mo.). BufferEZE formula 1 (transfer buffer) and X-OMat AR X-ray film were from Eastman Kodak Co. (Rochester, N.Y.). Maxosorb and Immunlon-1 microtiter plates were purchased from Nunc (Kamstrup, Denmark) and Dynatech (Chantilly, Va.), respectively. Cell culture plates (12-well) and culture media (with calf serum) were from Costar (Cambridge, Mass.) and Gibco (Grand Island, N.Y.), respectively. Polyethylene-20-sorbitan monolaurate (Tween-20) was from Fisher Biotech (Fair Lawn, N.J.). G25 Sephadex columns (PD-10) and $^{125}$I labeled Protein A were from Pharmacia (Piscataway, N.J.) and Amersham (Arlington Heights, Ill.), respectively. Bovine serum albumin (BSA) and rabbit IgG anti-human IgG (Fc-specific) were purchased from Cappel (Durham, N.C.) and Calbiochem (La Jolla, Calif.), respectively. Plasmid vector (pRK5), competent *E. coli* cells (DH5a and CJ236), synthetic oligonucleotides, cell culture medium, purified CHO-derived $VEGF_{165}$, monoclonal (Mates A4.6.1, 2E3, 4D7, SC3, and SF8) and polyclonal antibodies to $VEGF_{165}$ were prepared at Genentech, Inc. (South San Francisco, Calif.). Construction, expression and purification of FLT-1, flkl and KDR receptor-IgG chimeras was as described by Park, et al. *J. Biol. Chem.* 269, 25646-25654 (1994).

Site-directed Mutagenesis and Expression of VEGF Variants—Site-directed mutagenesis was performed using the Muta-Gene Phagemid in vitro mutagenesis kit according to the method of Kunkel *Proc. Natl. Acad. Sci.* 82, 488-492 (1985) and Kunkel et al., *Methods Enzymol.* 154, 367-382 (1987). A plasmid vector pRK5 containing cDNA for $VEGF_{165}$ isoform was used for mutagenesis and transient expression. The pRK5 vector is a modified pUC118 vector and contains a CMV enhancer and promoter [Nakamaye et al., *Nucleic Acids Res.* 14, 9679-9698 (1986) and Vieira et al., *Methods Enzymol.* 155, 3-11 (1987)]. The mutagenized DNA was purified using the Qiagen Plasmid Midi Kit Tip 100 and the sequence of the mutations was verified using Sequenase Version 2.0 Kit. The mutated DNA was analyzed by restriction enzyme digestion as described by Sambrook, et al., *Molecular Cloning: A Laboratory Manual* part I, C5.28-5.32, Cold Spring Harbor Laboratory Press, Cold Spring Harbor, N.Y. (1989).

Transient transfection of human fetal kidney "293 cells" was performed in 6-well plates using the modified calcium phosphate precipitate method as previously described [Jordan et al., *Bio/Technology (manuscript in preparation)* (1994); Chen et al., *Mol. Cell. Biol.* 7, 2745-2752 (1987); Gorman et al., *DNA and Protein Engineering Techniques* 2, 3-10 (1990); Graham et al., *Virology* 52, 456-467 (1973)]. Briefly, approximately $1.2 \times 10^6$ cells were incubated overnight at 37° C. in the presence of 15 µg of precipitated DNA. Cell culture supernatant was replaced with serum free medium, and cell monolayers were incubated for 72 hours at 37° C. Conditioned media (3 ml) was harvested, centrifuged, aliquoted and stored at −70° C. until use.

Quantitation of $VEGF_{165}$ Variants by ELISA—A radioimmunometric assay previously described [Aiello et al., *N. Engl. J. Med.* 331, 1480-1487 (1994)], was adapted for the quantitation of VEGF mutants by the following procedure. Individual wells of a 96-well microtiter plate were coated with 100 µl of a 3 µg/ml solution of an anti-$VEGF_{165}$ polyclonal antibody in 50 mM sodium carbonate buffer pH 9.6 overnight at 4° C. The supernatant was discarded, and the wells were washed 4 times with PBS containing 0.03% Tween 80. The plate was blocked in assay buffer (0.5% BSA, 0.03% Tween 80, 0.01% Thimerosal in PBS) for one hr (300 µl/well) at ambient temperature, then the wells were washed. Diluted samples (100 µl) and $VEGF_{165}$ standard (ranging from 0.1 to 10 ng/ml) were added to each well and incubated for one hr at ambient temperature with gentle agitation. The supernatant was discarded, and the wells were washed. Anti-VEGF murine monoclonal antibody 5F8 solution (100 µl at 1 µg/ml) was added, and the microtiter plate was incubated at ambient temperature for one hr with gentle agitation. After the supernatant was discarded, the plate was washed and horseradish peroxidase conjugated goat IgG specific for murine IgG (100 µl) at a dilution of 1:25000 was immediately added to each well. The plate was incubated for one hr at ambient temperature with gentle agitation after which the supernatant discarded, the wells washed, and developed by addition of orthophenylenediamine (0-04%), $H_2O_2$ (0.012%) in 50 mM citrate phosphate buffer pH 5 (100 µl), then incubated in the dark at ambient temperature for 10 min. The reaction was stopped by adding 50 µl of 4.5 N $H_2SO_4$ to each well and the absorbance was measured at 492 nm on a microplate reader (SLT Labs). The concentrations of $VEGF_{165}$ variants were quantitated by interpolation of a standard curve using non-linear regression analysis. For purposes of comparison, a second ELISA was developed that utilized a dual monoclonal format. The assay was similar to the above described ELISA, except a neutralizing monoclonal antibody (Mab A4.6.1) was used to coat the microtiter plates [Kim et al., *Growth Factors* 7, 53-64 (1992)].

Immunoblotting of VEGF mutants—Aliquots of conditioned cell media (16 µl) containing VEGF or VEGF mutant (approx. 10 ng) were added to 5×SDS sample buffer (4 µl) and heated at 90° C. for 3 min prior to loading on SDS polyacrylamide (4 to 20% acrylamide) gels. Pre-stained MW standards (10 µl) were loaded in the outer lanes of the SDS gels. Gels were run at 25 mA for 90 min at 4° C. Gels were transferred to nitrocellulose paper in a Bio-Rad tank blotter containing BufferEZE with 0.1% SDS for 90 min at 250 mA at 25° C. Nitrocellulose was pre-wetted in transfer buffer with 0.1% SDS for 10 min prior to use. Transferred immunoblots were blocked in PBS overnight with 1.0% BSA and 0.1% Tween 20 (blocking buffer) at 4° C. A solution containing 5 murine anti-VEGF Mabs (A.4.6.1, 5C3, 5F8, 4D7, and 2E3) was prepared with 2 µg/ml of each Mab in blocking buffer and used as primary antibody. The primary antibody solution was incubated with the immunoblots for 4 hr at 25° C. with gentle agitation, then washed 3× for 10 min in blocking buffer at 25° C. $^{125}$I labeled Protein A was diluted to $10^4$ cpm/ml (final concentration) in blocking buffer and incubated with the immunoblots for 60 min with gentle agitation at 25° C. Immunoblots were washed 3× for 10 min in blocking buffer at 25° C., then dried on filter paper and placed on Kodak X-Omat film with two intensifying screens at −70° C. for 3 days.

Preparation of $^{125}$I labeled $VEGF_{165}$—Radiolabeling of CHO-derived $VEGF_{165}$ was prepared using a modification of the chloramine T catalyzed iodination method [Hunter et al., *Nature* 194, 495-496 (1962)]. In a typical reaction, 10 µl of 1 M Tris-HCl, 0.01% Tween 20 at pH 7.5 was added to 5 µl of sodium iodide-125 (0.5 milliCuries, 0.24 nmol) in a capped reaction vessel. To this reaction, 10 µl of CHO-derived $VEGF_{165}$ (10 µg, 0.26 nmol) was added. The iodination was initiated by addition of 10 µl of 1 mg/ml chloramine T in 0.1 M sodium phosphate, pH 7.4. After 60 sec, iodination was terminated by addition of sodium metabisulfite (20 µl, 1 mg/ml) in 0.1 M sodium phosphate, pH 7.5. The reaction vessel was vortexed after each addition. The reaction mixture was applied to a PD-10 column (G25 Sephadex) that was pre-equilibrated with 0.5% BSA, 0.01% Tween 20 in PBS. Fractions were collected and counted for radioactivity with a gamma scintillation counter (LKB model 1277). Typically, the specific radioactivity of the iodinated VEGF was 26±2.5 µCi/µg, which corresponded to one $^{125}$I per two molecules of $VEGF_{165}$ dimer.

$VEGF_{165}$ Receptor Binding Assay—The assay was performed in 96-well immunoplates (Immulon-1); each well was coated with 100 µl of a solution containing 10 µg/ml of rabbit IgG anti-human IgG (Fc-specific) in 50 mM sodium carbonate buffer pH 9.6 overnight at 4° C. After the supernatant was discarded, the wells were washed three times in washing buffer (0.01% Tween 80 in PBS). The plate was blocked (300 μl/well) for one hr in assay buffer (0.5% BSA, 0.03% Tween 80, 0.01% Thimerosal in PBS). The supernatant was discarded and the wells were washed. A cocktail was prepared with conditioned cell media containing $VEGF_{165}$ mutants at varying concentrations (100 μl), $^{125}I$ radiolabeled $VEGF_{165}$ (approx. $5 \times 10_3$ cpm in 50 μl) which was mixed with VEGF receptor-IgG chimeric protein, FLT-1 IgG, flk-1 IgG or KDR-IgG (3-15 ng/ml, final concentration, 50 μl) in micronic tubes. Aliquots of this solution (100 μl) were added to pre-coated microtiter plates and incubated for 4 hr at ambient temperature with gentle agitation. The supernatant was discarded, the plate washed, and individual microtiter wells were counted by gamma scintigraphy (LKB model 1277). The competitive binding between unlabeled $VEGF_{165}$ (or $VEGF_{165}$ mutants) and $^{125}I$ radiolabeled $VEGF_{165}$ to the FLT-1, Flk-1, or KDR receptors were plotted, and analyzed using a four parameter fitting program (Kaleidagraph, Adelbeck Software). The apparent dissociation constant for each VEGF mutant was estimated from the concentration required to achieve 50% inhibition ($IC_{50}$).

Assay for Vascular Endothelial Cell Growth—The mitogenic activity of VEGF variants was determined by using bovine adrenal cortical endothelial (ACE) cells as target cells as previously described [Ferrara et al., *Biochem. Biophys. Res. Comm.* 161, 851-859 (1989)]. Briefly, cells were plated sparsely (7000 cells/well) in 12 well plates and incubated overnight in Dulbecco's modified Eagle's medium supplemented with 10% calf serum, 2 mM glutamine, and antibiotics. The medium was exchanged the next day, and VEGF or VEGF mutants, diluted in culture media at concentrations ranging from 100 ng/ml to 10 pg/ml, were layered in duplicate onto the seeded cells. After incubation for 5 days at 37° C., the cells were dissociated with trypsin, and quantified using a Coulter counter.

Isolation of VEGF cDNA

Total RNA was extracted [Ullrich et al., *Science* 196, 1313-1317 (1977)] from bovine pituitary follicular cells [obtained as described by Ferrara et al., *Meth. Enzymol.* supra, and Ferrara et al., *Am. J. Physiol.*, supra] and the polyadenylated mRNA fraction was isolated by oligo(dT)-cellulose chromatography. Aviv et al., *Proc. Natl. Acad. Sci. USA* 69, 1408-1412 (1972). The cDNA was prepared [Wickens et al., *J. Biol. Chem.* 253, 2483-2495 (1978)] by priming with $dT_{12-18}$ or a random hexamer $dN_6$. The double-stranded cDNA was synthesized using a cDNA kit from Amersham, and the resulting cDNA was subcloned into EcoRI-cleaved Igt10 as described [Huynh et al., *DNA Cloning Techniques, A Practical Approach*, Glover ed. (IRL, Oxford, 1985)], except that asymmetric EcoRI linkers [Norris et al., *Gene* 7, 355-362 (1979)] were used, thus avoiding the need for the EcoRI methylase treatment.

The recombinant phage were plated on *E. coli* C600 Hfl [Huynh et al. supra] and replica plated onto nitrocellulose filters. Benton et al., *Science* 196, 180-182 (1977). These replica were hybridized with a $^{32}P$-labeled [Taylor et al., *Biochim. Biophys. Acta,* 442, 324-330 (1976)] synthetic oligonucleotide probe of the sequence: 5'-CCTATGGCT-GAAGGCGGCCAGAAGCCTCACGAAGTG-GTGAAGTTCATGGACGTGTATCA-3' (SEQ ID NO: 3) at 42° C. in 20% formamide, 5×SSC, 50 mM sodium phosphate pH 6.8, 0.1% sodium pyrophosphate, 5× Denhardt's solution, and 50 mg/ml salmon sperm DNA, and washed in 2×SSC, 0.1% SDS at 42° C.

One positive clone, designated I.vegf.6, was identified. This clone, labeled with $^{32}p$, was used as a probe to screen an oligo-dT-primed human placenta cDNA library, and positive clones were observed. When a human pituitary cDNA library was screened with the same labeled clone, no positive clones were detected.

The complete nucleotide sequence of the clone I.vegf.6 was determined by the dideoxyoligonucleotide chain termination method [Sanger et al., *Proc. Natl. Acad. Sci. USA* 74, 5463-5467 (1977)] after subcloning into the pRK5 vector. The sequence obtained, along with the imputed amino acid sequence, including the signal sequence.

Expression of VEGF-Encoding Gene in Mammalian Cells

The final expression vector, pRK5.vegf.6, was constructed from I.vegf.6 and pRK5. The construction of pRK5 and pRK5.vegf.6 is described below in detail.

A. Construction of pRK5

A.1. Construction of pF8CIS

The initial three-part construction of the starting plasmid pF8CIS is described below.

1) The ampicillin resistance marker and replication origin of the final vector was derived from the starting plasmid pUC13 pML, a variant of the plasmid pML (Lusky, M. and Botchen, M., *Nature,* 293, 79 [1981]). pUC13pML was constructed by transferring the polylinker of pUC13 (Vieira, J. and Messing, J., *Gene,* 19, 259 (1982) to the EcoRI and HindIII sites of pML. A second starting plasmid pUC8-CMV was the source of the CMV enhancer, promoter and splice donor sequence. pUC8-CMV was constructed by inserting approximately 800 nucleotides for the CMV enhancer, promoter and splice donor sequence into the blunted PstI and SphI sites of pUC8. Vieira, J. and Messing, J., op. cit. Synthetic BamHI-HindIII linkers (commercially available from New England Biolabs) were ligated to the cohesive BamHI end creating a HindIII site. Following this ligation a HindIII-HincII digest was performed. This digest yielded a fragment of approximately 800 bp that contained the CMV enhancer, promoter and splice donor site. Following gel isolation, this 800 bp fragment was ligated to a 2900 bp piece of pUC13 pML. The fragment required for the construction of pF8CIS was obtained by digestion of the above intermediate plasmid with SalI and HindIII. This 3123 bp piece contained the resistance marker for ampicillin, the origin of replication from pUC13 pML, and the control sequences for the CMV, including the enhancer, promoter, and splice donor site.

2) The Ig variable region intron and splice acceptor sequence was constructed using a synthetic oligomer. A 99 mer and a 30 mer were chemically synthesized having the following sequence for the IgG intron and splice acceptor site (Bothwell et al., *Nature,* 290, 65-67 ]1981]):

```
1    5' AGTAGCAAGCTTGACGTGTGGCAGGCTTGA. . .

31   GATCTGGCCATACACTTGAGTGACAATGA. . .

60   CATGCACTTTGCCTTTCTCTCCACAGGT. . .
```

```
            -continued
88   GTCCAGTCCCAG 3' (SEQ ID NO:4)

1   3' CAGGTGAGGGTGCAGCTTGACGTCGTCGGA 5'
    (SEQ ID NO:5)
```

DNA polymerase I (Klenow fragment) filled in the synthetic piece and created a double-stranded fragment. Wartell, R. M. and W. S. Reznikoff, Gene, 9, 307 (1980). This was followed by a double digest of PstI and HindIII. This synthetic linker was cloned into pUC13 (Veira and Messing, op. cit.) at the PstI and HindIII sites. The clones containing the synthetic oligonucleotide, labeled pUClg. 10, was digested with PstI. A ClaI site was added to this fragment by use of a PstI-ClaI linker. Following digestion with HindIII a 118-bp piece containing part of the Ig intron and the Ig variable region splice acceptor was gel isolated.

3) The third part of the construction scheme replaced the hepatitis surface antigen 3' end with the polyadenylation site and transcription termination site of the early region of SV40. A vector, pUC.SV40, containing the SV40 sequences was inserted into pUC8 at the BamHI site described by Vieira and Messing, op. cit. pUC.SV40 was then digested with EcoRI and HpaI. A 143 bp fragment containing the SV40 polyadenylation sequence was gel isolated from this digest. Two additional fragments were gel isolated following digestion of pSVE.8c1D. (European Pat. Pub. No. 160,457). The 4.8 kb fragment generated by EcoRI and Cla 1 digestion contains the SV40-DHFR transcription unit, the origin of replication of pML and the ampicillin resistance marker. The 7.5-kb fragment produced following digestion with ClaI and HpaI contains the cDNA for Factor VIII. A three-part ligation yielded pSVE.8c24D. This intermediate plasmid was digested by ClaI and SalI to give a 9611 bp fragment containing the cDNA for Factor VIII with an SV40 poly A site followed by the SV40 DHFR transcription unit.

The final three-part ligation to yield pF8CIS used: a) the 3123 bp SalI-HindIII fragment containing the origin of replication, the ampicillin resistance marker, and the CMV enhancer, promoter, and splice donor site; b) the 118 bp HindIII-ClaI fragment containing the Ig intron and splice acceptor site; and c) a 9611 bp ClaI-SalI fragment containing the cDNA for Factor VIII, the SV40 polyadenylation site, and the SV40 DHFR transcription unit.

A.2. Construction of pCIS2.8c28D pCIS2.8c28D comprises a 90 kd subunit of Factor VIII joined to a 73 kd subunit of Factor VIII. The 90 kd comprises amino acids 1 through 740 and the 73 kd subunit amino acids 1690 through 2332. This construct was prepared by a three-part ligation of the following fragments: a) the 12617-bp ClaI-SstII fragment of pF8CIS (isolated from a dam-strain and BAP treated); b) the 216-bp SstII-PstI fragment of pF8CIS; and c) a short PstI-ClaI synthetic oligonucleotide that was kinased.

Figure 4:
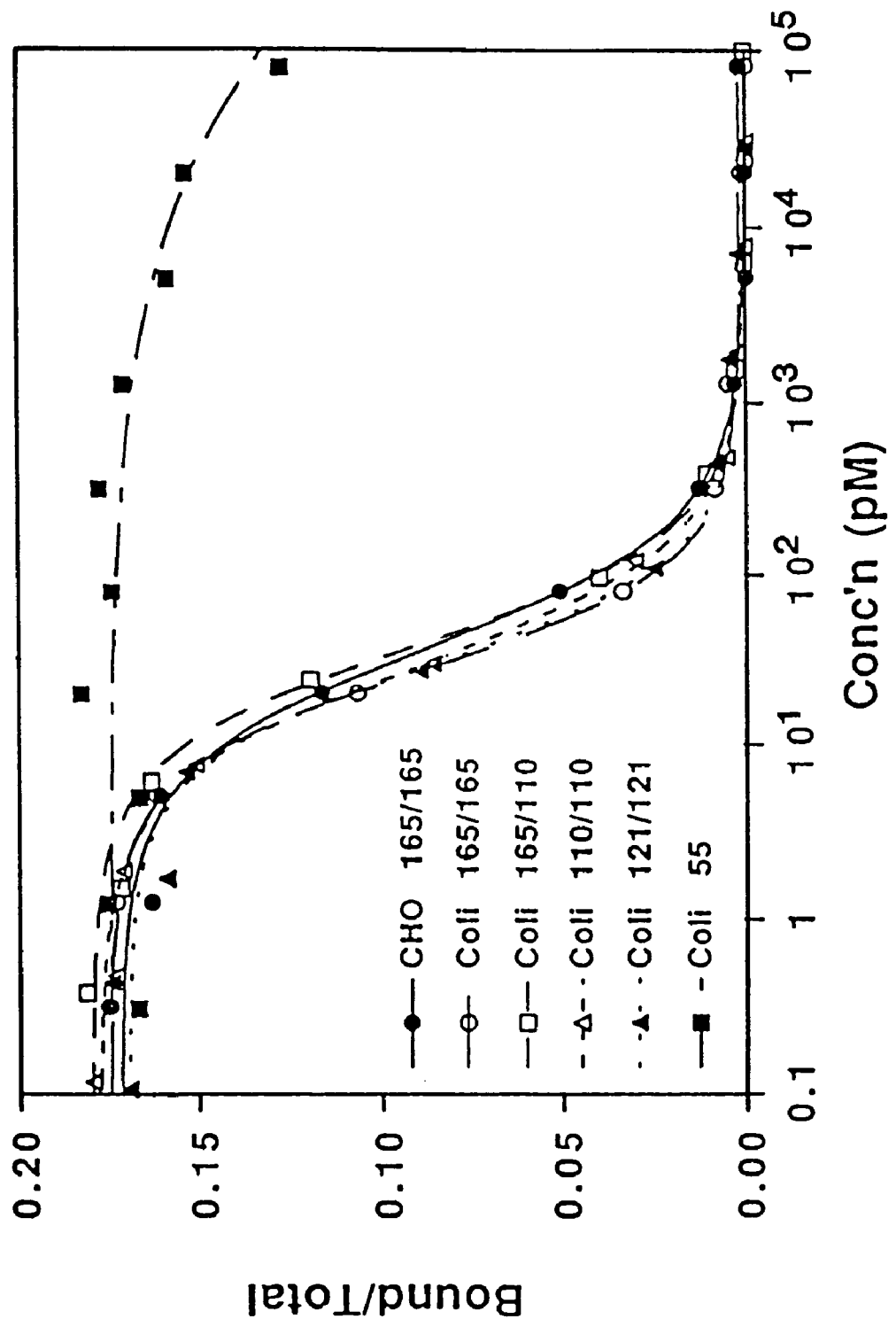
FIG. 4 shows the KDR receptor binding being mediated by the 1-110 dimer of VEGF.

FIG. 4 also shows the subcloning of the 408 bp BamHI-HindIII and the 416 bp BamHI-PstI fragments of pSVEFVIIII (European Pat. Publ. No. 160,457) containing the 5' and 3' DNA regions of Factor VIII to be fused to make pCIS2.8c28D.

FIG. 5 shows the three-part ligation used to construct the fusion region of pCIS2.8c28D. Two different fragments, A and B, were cloned into the same pUC118 BamHI-PstI BAP vector. The A fragment was the 408 bp BamHI-HindIII fragment of pUC408BH and the B fragment was a HindIII-PstI oligonucleotide. This oligonucleotide was used without kinasing to prevent its polymerization during ligation.

After ligation of the A and B fragments into the vector, the expected junction sequences were confirmed by DNA sequencing of the regions encompassed by the nucleotides.

The resulting plasmid, pCIS2.8c28D, was constructed with a four-part ligation. The fusion plasmid was cut with BamHI and PstI and the 443 bp fragment isolated. The remaining three fragments of the four-part ligation were: 1) 1944 bp ClaI-BamHI of pSVEFVIII (European Pat. Publ. No. 160,457); 2) a 2202 bp BamHI-XbaI fragment of pSVEFVIII, which was further partially digested with PstI and the 1786 bp PstI-XbaI fragment was isolated, and 3) the 5828 bp XbaI-ClaI BAP fragment of pCIS2.8c24D. The translated DNA sequence of the resultant variant in the exact fusion junction region of pCIS2.8c28D was determined and correlates.

A.3. Construction of pRK5

The starting plasmid for construction of pRK5 was pCIS2.8c28D. The base numbers in paragraphs 1 through 6 refer to pCIS2.8c28D with base one of the first T of the EcoRI site preceding the CMV promoter. The cytomegalovirus early promoter and intron and the SV40 origin and polyA signal were placed on separate plasmids.

1. The cytomegalovirus early promoter was cloned as an EcoRI fragment from pCIS2.8c28D (9999-1201) into the EcoRI site of pUC118 described above. Twelve colonies were picked and screened for the orientation in which single-stranded DNA made from pUC118 would allow for the sequencing from the EcoRI site at 1201 to the EcoRI site at 9999. This clone was named pCMVE/P.

2. Single-stranded DNA was made from pCMVE/P in order to insert an SP6 (Green, M R et al., Cell 32, 681-694 [1983]) promoter by site-directed mutagenesis. A synthetic 110 mer that contained the sequences from −69 to +5 of SP6 promoter (see Nucleic Acids Res., 12, 7041 [1984]) were used along with 18-bp fragments on either end of the oligomer corresponding to the CMVE/P sequences. Mutagenesis was done by standard techniques and screened using a labeled 110 mer at high and low stringency. Six potential clones were selected and sequenced. A positive clone was identified and labeled pCMVE/PSP6.

3. The SP6 promoter was checked and shown to be active, for example, by adding SP6 RNA polymerase and checking for RNA of the appropriate size.

4. A ClaI-NotI-Sma adapter was synthesized to encompass the location from the ClaI site (912) to the SmaI site of pUC118 in pCMVE/P (step 1) and pCMVE/PSP6 (step 2). This adapter was ligated into the ClaI-SmaI site of pUC118 and screened for the correct clones. The linker was sequenced in both and clones were labeled pCMVE/PSP6-L and pCMVE/P-L.

5. pCMVE/PSP6-L was cut with SmaI (at linker/pUC118 junction) and HindIII (in pUC118). A HpaI (5573)-to-HindIII (6136) fragment from pSVORAADRI 11, described below, was inserted into SmaI-HindIII of pCMVE/PSP6-L. This ligation was screened and a clone was isolated and named pCMVE/PSP6-L-SVORAADRI.

a) The SV40 origin and polyA signal was isolated as the XmnI (5475)-HindIII (6136) fragment from pCIS2.8c28D and cloned into the HindIII to SmaI sites of pUC119 (described in Vieira and Messing, op. cit.). This clone was named pSVORAA.

b) The EcoRI site at 5716 was removed by partial digestion with EcoRI and filling in with Klenow. The colonies obtained from self-ligation after fill-in were screened and the correct clone was isolated and named pSVORAADRI 11. The deleted EcoRI site was checked by sequencing and shown to be correct.

c) The HpaI (5573) to HindIII (6136) fragment of pSVORAADRI 11 was isolated and inserted into pCMVE/PSP6-L (see 4 above).

6. pCMVE/PSP6-L-SVOrAADRI (step 5) was cut with EcoRI at 9999, blunted and self-ligated. A clone without an EcoRI site was identified and named pRK.

7. pRK was cut with SmaI and BamHI. This was filled in with Klenow and relegated. The colonies were screened. A positive clone was identified and named pRKDBam/Sma3.

8. The HindIII site of pRKDBam/Sma3 was converted to a HpaI site using a converter. (A converter is a piece of DNA used to change one restriction site to another. In this case one end would be complementary to a HindIII sticky end and the other end would have a recognition site for HpaI.) A positive clone was identified and named pRKDBam/Sma, HIII-HpaI 1.

9. pRKDBam/Sma, HIII-HpaI 1 was cut with PstI and NotI and an EcoRI-HindIII linker and HindIII-EcoRI linker were ligated in. Clones for each linker were found. However, it was also determined that too many of the HpaI converters had gone in (two or more converters generate a PvuII site). Therefore, these clones had to be cut with HpaI and self-ligated.

10. RI-HIII clone 3 and HIII-RI clone 5 were cut with HpaI, diluted, and self-ligated. Positives were identified. The RI-HIII clone was named pRK5.

B. Construction of pRK5.vegf.6

The clone I.vegf.6 was treated with EcoRI and the EcoRI insert was isolated and ligated into the vector fragment of pRK5 obtained by digestion of pRK5 with EcoRI and isolation of the large fragment. The two-part ligation of these fragments yielded the expression vector, pRK5.vegf.6, which was screened for the correct orientation of the VEGF-encoding sequence with respect to the promoter.

Further details concerning the construction of the basic pRK5 vector can be taken from U.S. Pat. No. 5,332,671 that issued on 26 Jul. 1994.

EXAMPLE 2

Figure 13:
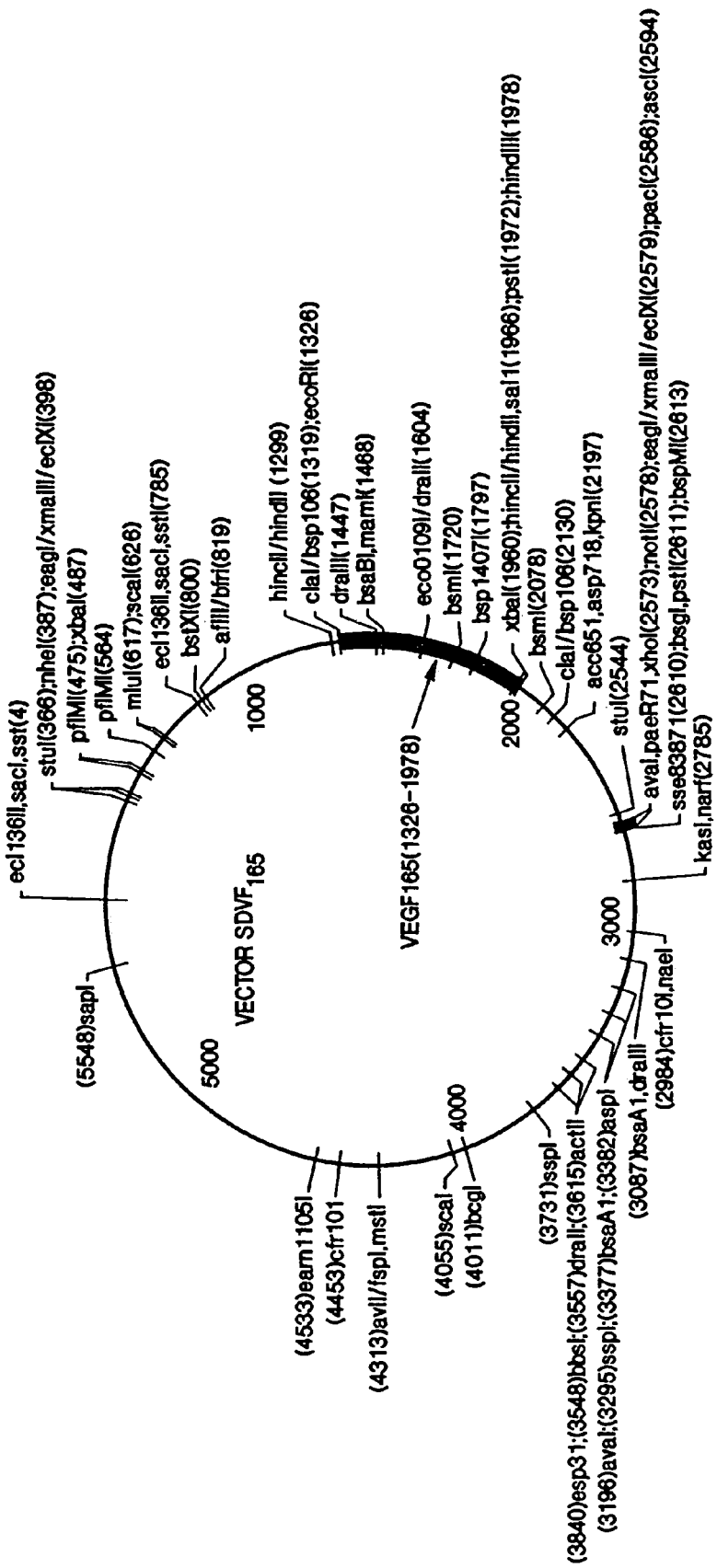
FIG. 13 depicts the construction with its various elements of the plasmid $pSDVF_{165}$.
Figure 14:
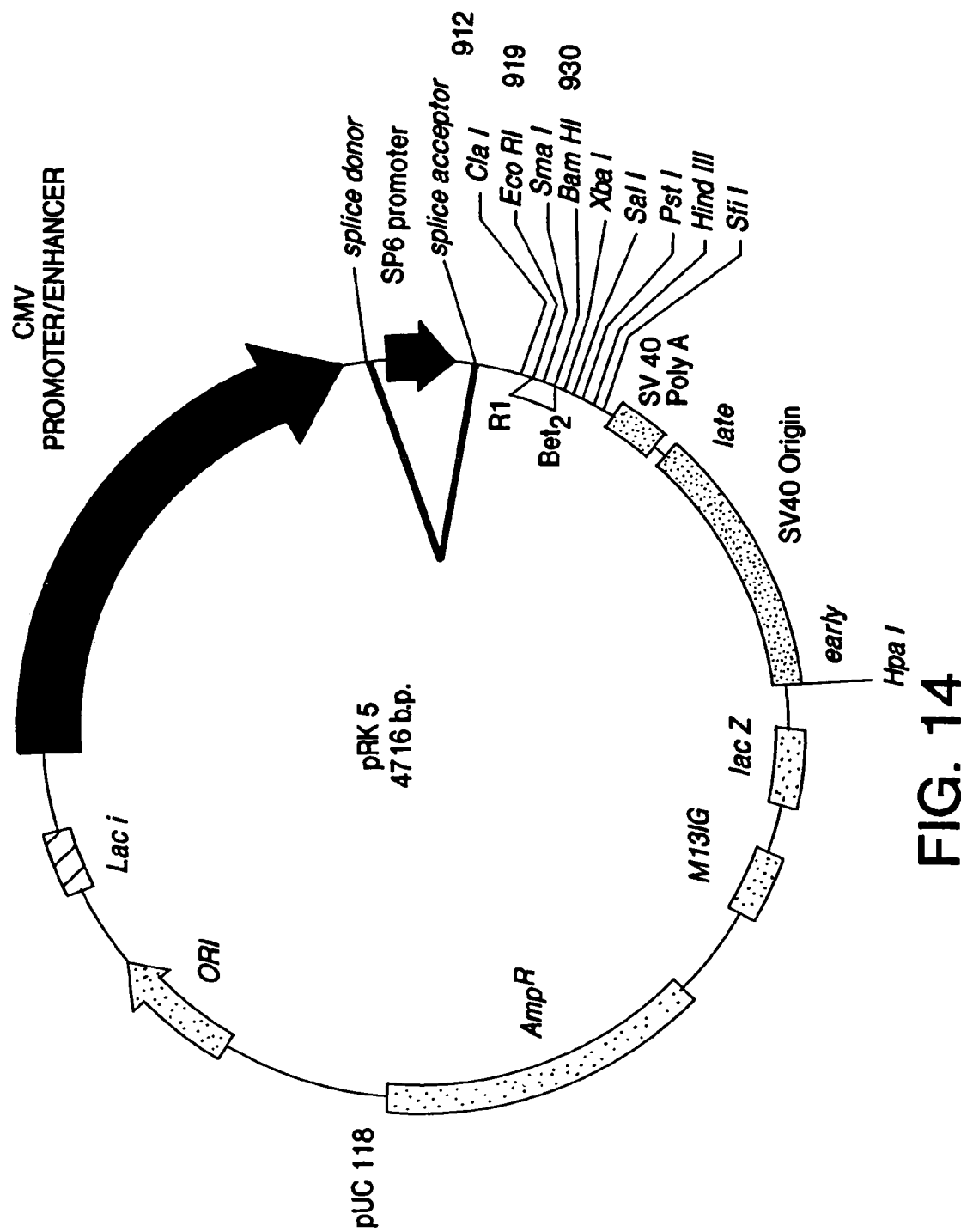
FIG. 14 depicts the construction with its various elements of the plasmid pRK5.
Figure 15:
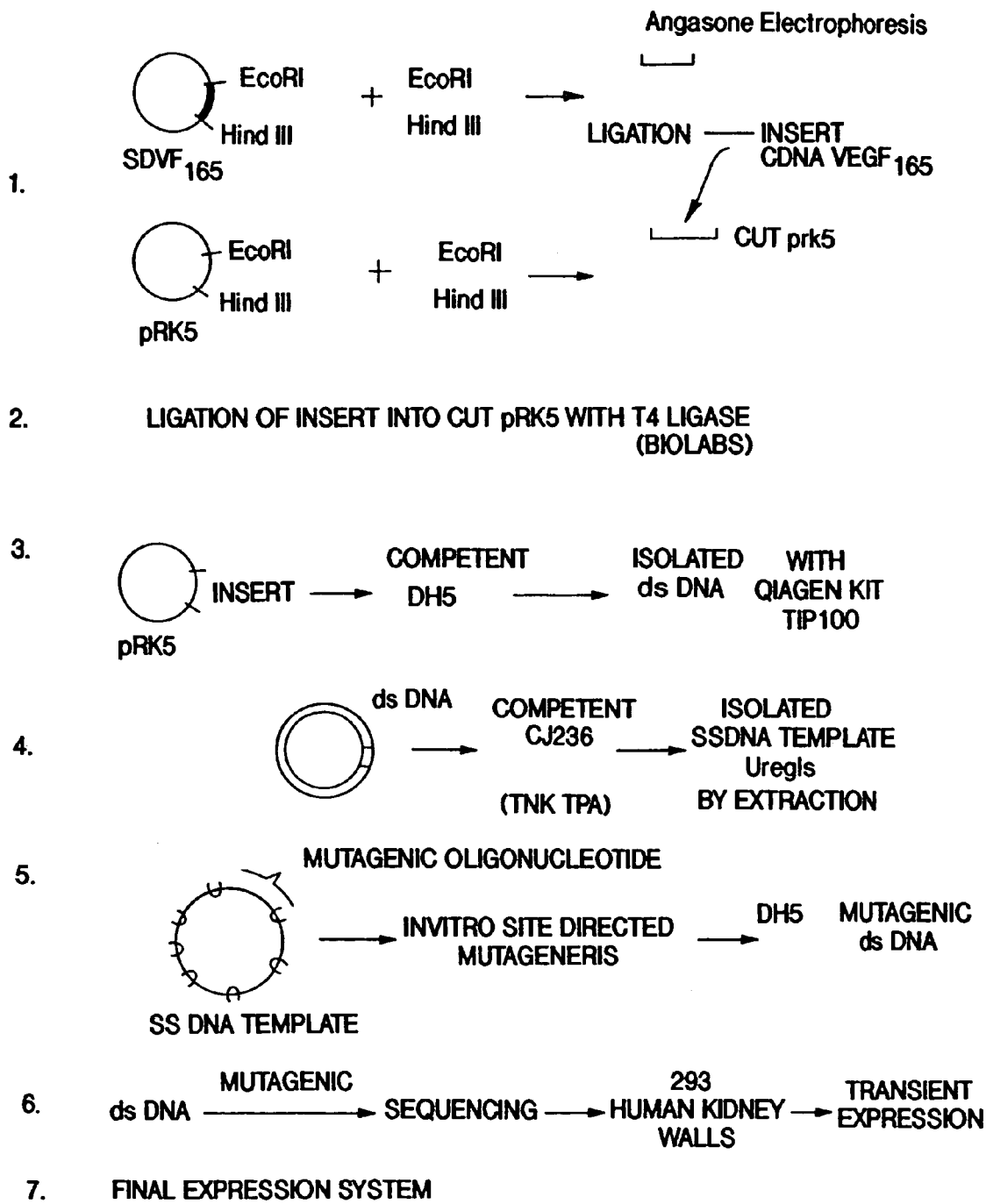
FIG. 15 depicts the construction schematic followed to prepare the final expression vectors harboring DNA that contains mutations in accordance with preparing the various products of the present invention.

The following example details the methodology generally employed to prepare the various mutants covered by the present invention. The basic expression vector was prepared as follows:

Vector $SDVF_{165}$ containing the cDNA of $VEGF_{165}$ was obtained and is depicted in FIG. 13 herein. The cDNA for $VEGF_{165}$ was isolated from $SDVF_{165}$ by restriction digestion with Hind III and Eco RI. This isolated insert was ligated into the pRK5 plasmid taking advantage to the existence therein of Eco RI and Hind III sites—see the construct as depicted in FIG. 14 hereof. The resultant plasmid was transformed into competent CJ236 E. coli cells to make a template for site-directed mutagenesis. The corresponding oligonucleotide containing the mutated site was then prepared—see infra—and the in vitro site-directed mutagenesis step was conducted in accordance with known procedures using the BioRad Muta-Gene mutagenesis kit. After sequencing to determine that the mutagenesized site was incorporated into the final expression vector, the resultant vector was transfected into 293 human kidney cells for transient expression. Reference is made to FIG. 15 which provides a general depiction of the construction of such expression vectors.

The following oligonucleotides were prepared in order to make the final mutated product. Table 2 provides such information.

TABLE 2

| MUTATION | 5'-3' SEQUENCE | SEQ ID NO. |
|---|---|---|
| E5A | CCCTCCTGCGGCTGCCATGGGTGC | 6 |
| H11A, H12A, E13A | CTTCACCACGGCGGCGGCATTCTGCCCTCC | 7 |
| K16A, D19A | CTGATAGACGGCCATGAAGGCCACCACTTCGTG | 8 |
| R23A | GCAGTAGCTGGCCTGATAGACATC | 9 |
| H27A, E30A | CACCAGGGTGGCGATTGGGGCGCAGTAGCTGCG | 10 |
| D34A, E38A | ATCAGGGTAGGCCTGGAAGATGGCCACCAGGGTCTC | 11 |
| D41A, E42A, E44A | GAAGATGTAGGCGATGGCGGCAGGGTACTCCTG | 12 |
| K48A | ACAGGATGGGGCGAAGATGTACTC | 13 |
| R5GA | GCCCCCGCAGGCCATCAGGGGCAC | 14 |
| D63, AE64, AE67A | GGGCACACAGGCCAGGCCGGCGGCATTGCAGCAGCC | 15 |
| E72A, E73A | GATGTTGGAGGCGGCAGTGGGCAGACA | 16 |
| R82A, K84A, H86A | CTGGCCTTGGGCAGGGGCGATGGCCATAATCTGCAT | 17 |
| H90A, E93A | GAAGCTCATGGCTCCTATGGCCTGGCCTTGGTG | 18 |
| H99A, K101A | GCATTCACAGGCGTTGGCCTGTAGGAAGCT | 19 |

TABLE 2-continued

| MUTATION | 5'-3' SEQUENCE | SEQ ID NO. |
|---|---|---|
| E103A | TGGTCTGCAGGCACATTTGTTGTG | 20 |
| K107A, K108A, D109A, R110A | TTGTCTTGCGGCGGCGGCGGCTGGTCTGCATTC | 21 |
| K107A, K108A | TGCTCTATCGGCGGCTGGTCTGCATTC | 22 |
| D109A, R110A | TTGTCTTGCGGCGGCTTTCTTTGGTCT | 23 |
| R105A | TTTCTTTGGGGCGCATTCACATTT | 24 |
| R112A, E114A | ACAGGGATTGGCTTGGGCTGCTCTATCTTT | 25 |
| N75A | CATGGTGATGGCGGACTCCTCAGT | 26 |
| H12T | CACCACTTCGGTATGATTCTGCCC | 27 |
| E64T | CTCCAGGCCGGTGTCATTGCAGCA | 28 |
| D143T | GCAACGCGAGGTTGTGTTTTTGCA | 29 |
| R156T | TCTGCAAGTGGTTTCGTTTAACTC | 30 |
| H11A | CACCACTTCGTGGGCATTCTGCCCTCC | 31 |
| H12A | CTTCACCACTTCGGCATGATTCTGCCC | 32 |
| E13A | GAACTTCACCACGGCGTGATGATTCTG | 33 |
| K16A | GAGATCCATGAAGGCCACCACTTCGTG | 34 |
| D19A | GCGCTGATAGACGGCCATGAACTTCACCAC | 35 |
| H27A | GGTCTCGATTGGGGCGCAGTAGCTGCG | 36 |
| D34A | CTCCTGGAAGATGGCCACCAGGGTCTC | 37 |
| E38A | CTCATCAGGGTAGGCCTGGAAGATGTC | 38 |
| D41A | GTAATCGATCTCGGCAGGGTACTCCTG | 39 |
| E30A | GTCCACCAGGGTGGCGATTGGATGGCA | 40 |
| E42A | GATGTACTCGATGGCATCAGGGTACTC | 41 |
| E44A | CTTGAAGATGTAGGCGATCTCATCCAG | 42 |

Thus prepared in accordance with the insertion of the oligonucleotides set forth in Table 2 above, left column there are prepared at the corresponding mutation in the VEGF molecule in accordance with the notation given under the left hand column entitled "Mutation". The naming of the compound is in accord with naming convention. Thus, for the first entry the mutation is referred to as "E5A". This means that at the 5 position of the VEGF molecule the glutamic acid (E) was mutated so as to insert an alanine (A) at that 5 position.

In accordance with the foregoing the following mutations were also inserted into the VEGF molecule.

TABLE 3

| MUTATIONS |
|---|
| N62A |
| G65A |
| L66A |
| M78A |
| Q79A |
| I80A |
| M81A |

TABLE 3-continued

| MUTATIONS |
|---|
| I83A |
| P85A |
| Q87A |
| G88A |
| Q89A |
| I91A |
| G92A |
| H27A |
| D63K |
| E64R |
| E67K |
| D63K, E64R, E67K |
| R82E |
| K84E |
| H86E |
| R82E, K84E, H86E |

The effects of such site-directed mutations in the VEGF molecule are set forth in Tables 4 and 5 hereof:

TABLE 4

| Variants of Human VEGF | | Half-Maximal Inhibitory Concentration (ng/ml) | | Half-Maximal Effective Concentration (ng/ml) Endothelial |
|---|---|---|---|---|
| Mean | Mutation | KDR-IgG | FLT-IgG | Cells |
| 63 | D63A | 0.18 | 1.54 | 2.47 |
| 64 | E64A | 8.0 | 0.94 | 1.65 |
| 64 | E64S | | 1.90 | 6.25 |
| 64.7 | D63A, E64A, E67A | 2.8 | 44.6 | 1.05 |
| 65 | E64N, L66S | | 35.6 | 2.70 |
| 67 | E67A | 0.61 | 0.47 | 1.99 |
| 82 | R82A | 0.87 | 1.23 | 1.95 |
| 83 | RIK(82-84)NLS | >10000 | 1.63 | >100 |
| 84 | K84A | 6.3 | 1.91 | 2.00 |
| 84 | R82A, K84A, H86A | 1340 | 1.70 | 19.8 |
| 86 | H86A | 2.0 | 1.19 | 1.75 |
| WT | VEGF (CHO cell) | 1.32 | 0.95 | 0.54 |
| WT | VEGF (293 cell) | 1.14 | | 1.08 |

Mean residue number
Boldface sequence indicates mutations that potentially alter VEGF glycosylation

TABLE 5

| Variants of Human VEGF | | Half-Maximal Inhibitory Concentration (ng/ml) | | Half-Maximal Effective Concentration (ng/ml) Endothelial |
|---|---|---|---|---|
| Mean | Mutation | KDR-IgG | FLT-IgG | Cells |
| 5 | E5A | | | 0.88 |
| 12 | H11A, H12A, E13A | 1.2 | 0.62 | 2.55 |
| 17.5 | K16A, D19T | 2.1 | 0.73 | 2.05 |
| 23 | R23A | 2.0 | 1.0 | 2.40 |
| 27 | H27A | na. | na. | na. |
| 30 | E30A | | | 0.92 |
| 34 | D34A | 0.54 | 0.59 | 1.23 |
| 38 | E38A | 0.41 | 0.87 | 0.95 |
| 41 | D41A | | | 0.65 |
| 42 | E42A | 0.26 | 0.51 | 0.77 |
| 43 | E42N, E44S | 0.59 | 0.77 | 1.00 |
| 44 | E44A | 0.17 | 0.54 | 0.49 |
| 48 | K48A | 0.77 | 1.08 | 1.09 |
| 56 | R56A | na. | na. | na. |
| 72.5 | E72A, E73A | 1.3 | 0.91 | 1.75 |
| 75 | N75A | | 1.26 | 0.44 |
| 91.5 | H90A, E93A | 1.3 | .077 | 1.28 |
| 100 | H99A, K101A | 1.26 | 1.33 | 1.25 |
| 103 | E103A | 2.34 | 0.74 | 1.25 |
| 105 | R105A | 1.63 | 1.57 | 3.20 |
| 107.5 | K107A, K108A | 2.99 | 2.94 | 0.95 |
| 108.5 | KKDR(107-110)AAAA | 2.94 | 2.42 | 1.00 |
| 109.5 | D109A, R110A | 1.17 | 1.42 | |
| 113 | R112A, E114A | 1.52 | 0.56 | 1.10 |
| WT | VEGF (CHO cell) | 1.32 | 0.95 | 0.54 |
| WT | VEGF (293 cell) | 1.14 | | 1.08 |

Mean residue number
Boldface sequence indicates mutations that potentially alter VEGF glycosylation The data presented supra in Tables 4 and 5 may also be expressed as pM half-maximal inhibitory concentration and pM half-maximal effective concentration as set forth in Table 6:

TABLE 6
Effects of Site-Directed Mutations in VEGF

| Variants of Human VEGF | | Half-Maximal Inhibitory[1] Concentration (pM) | | Half-Maximal Effective Concentration (pM) Endothelial |
|---|---|---|---|---|
| Mean[2] | Mutation[3] | KDR-IgG | FLT-IgG | Cells |
| 5 | E5A | 37 ± 1 | 22 ± 1 | 23 ± 2 |
| 12 | H11A, H12A, E13A | 31 ± 2 | 20 ± 1 | 61 ± 6 |
| 17.5 | K16A, D19T | 26 ± 3 | 19 ± 1 | 53 ± 14 |
| 23 | R23A | 51 ± 1 | 30 ± 2 | 63 ± 5 |
| 27 | H27A | n.a. | n.a. | n.a. |
| 30 | E30A | 29 ± 1 | 28 ± 1 | 24 ± 1 |
| 34 | D34A | 14 ± 4 | 11 ± 2 | 30 ± 1 |
| 38 | E38A | 11 ± 1 | 15 ± 2 | 29 ± 8 |
| 41 | D41A | 36 ± 1 | 22 ± 1 | 17 ± 1 |
| 42 | E42A | 7 ± 1 | 8 ± 1 | 20 ± 3 |
| 43 | E42N, E44S | 15 ± 1 | 13 ± 1 | 27 ± 14 |
| 44 | E44A | 4 ± 1 | 9 ± 1 | 13 ± 1 |
| 48 | K48A | 20 ± 10 | 26 ± 1 | 29 ± 6 |
| 56 | R56A | n.a. | n.a. | n.a. |
| 63 | D63A | 5 ± 2 | 26 ± 1 | 64 ± 23 |
| 64 | E64A | 208 ± 5 | 16 ± 1 | 43 ± 5 |
| 64.7 | D63A, E64A, E67A | 73 ± 9 | 780 ± 120 | 24 ± 4 |
| 65 | E64N, L66S | 153 ± 11 | 980 ± 5 | 82 ± 12 |
| 67 | E67A | 16 ± 1 | 8 ± 1 | 52 ± 19 |
| WT | VEGF (CHO cell) | 28 ± 1 | 19 ± 1 | 16 ± 8 |
| WT | VEGF (293 cell) | 30 ± 4 | 22 ± 2 | 28 ± 10 |
| 72.5 | E72A, E73A | 33 ± 1 | 30 ± 2 | 46 ± 12 |
| 75 | N75A | 23 ± 17 | 22 ± 1 | 11 ± 2 |
| 82 | R82A | 32 ± 3 | 20 ± 1 | 38 ± 9 |
| 83 | RIK(82-84)NLS | >100000 | 29 ± 5 | >2000 |
| 84 | K84A | 167 ± 6 | 24 ± 3 | 54 ± 5 |
| 84 | R82A, K84A, H86A | >10000 | 48 ± 3 | 520 ± 150 |
| 86 | H86A | 53 ± 1 | 15 ± 1 | 43 ± 13 |
| 91.5 | H90A, E93A | 34 ± 1 | 26 ± 1 | 33 ± 8 |
| 100 | H99A, K101A | 34 ± 5 | 30 ± 3 | 33 ± 1 |
| 103 | E103A | 61 ± 4 | 17 ± 1 | 33 ± 6 |
| 105 | R105A | 42 ± 5 | 38 ± 1 | 84 ± 34 |
| 107.5 | K107A, K108A | 78 ± 7 | 66 ± 3 | 25 ± 6 |
| 108.5 | KKDR(107-110)AAAA | 77 ± 4 | 54 ± 5 | 26 ± 3 |
| 109.5 | D109A, R110A | 30 ± 3 | 35 ± 1 | 20 ± 1 |
| 113 | R112A, E114A | 40 ± 2 | 13 ± 2 | 29 ± 5 |
| WT | VEGF (CHO cell) | 28 ± 1 | 19 ± 1 | 16 ± 8 |
| WT | VEGF (293 cell) | 30 ± 4 | 22 ± 2 | 28 ± 10 |

[1]The values for IC50 in the KDR-IgG and FLT-IgG binding studies are in the absence of heparin (15 µg/ml). Errors associated with these values are ±S.E.M.
[2]Mean residue number indicates the average position of the mutation(s).
[3]Boldface sequence indicates mutations that potentially alter VEG glycosylation.

Figure 16:
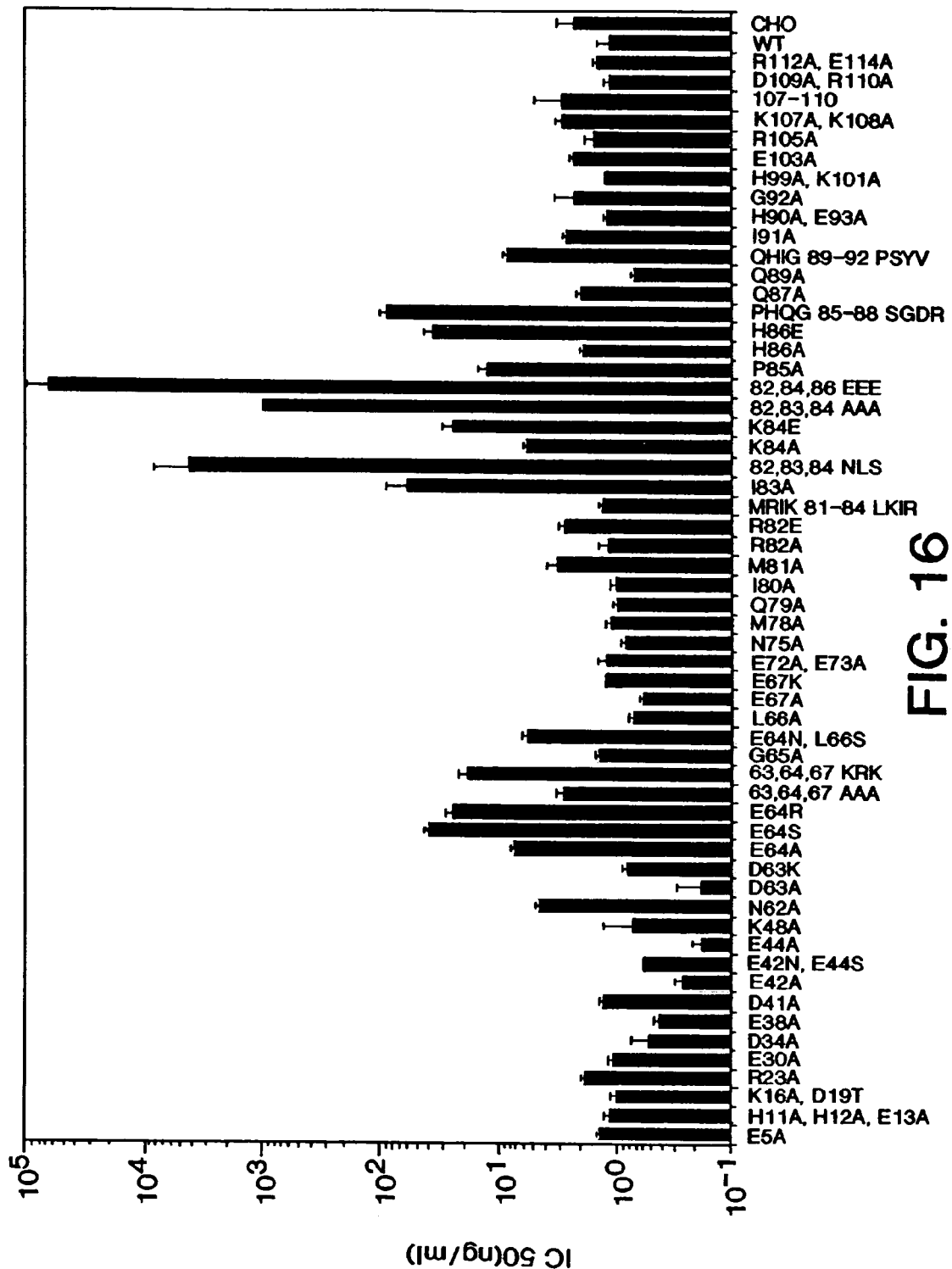
FIG. 16 depicts the KDR-IgG binding levels of various VEGF variants.
Figure 17:
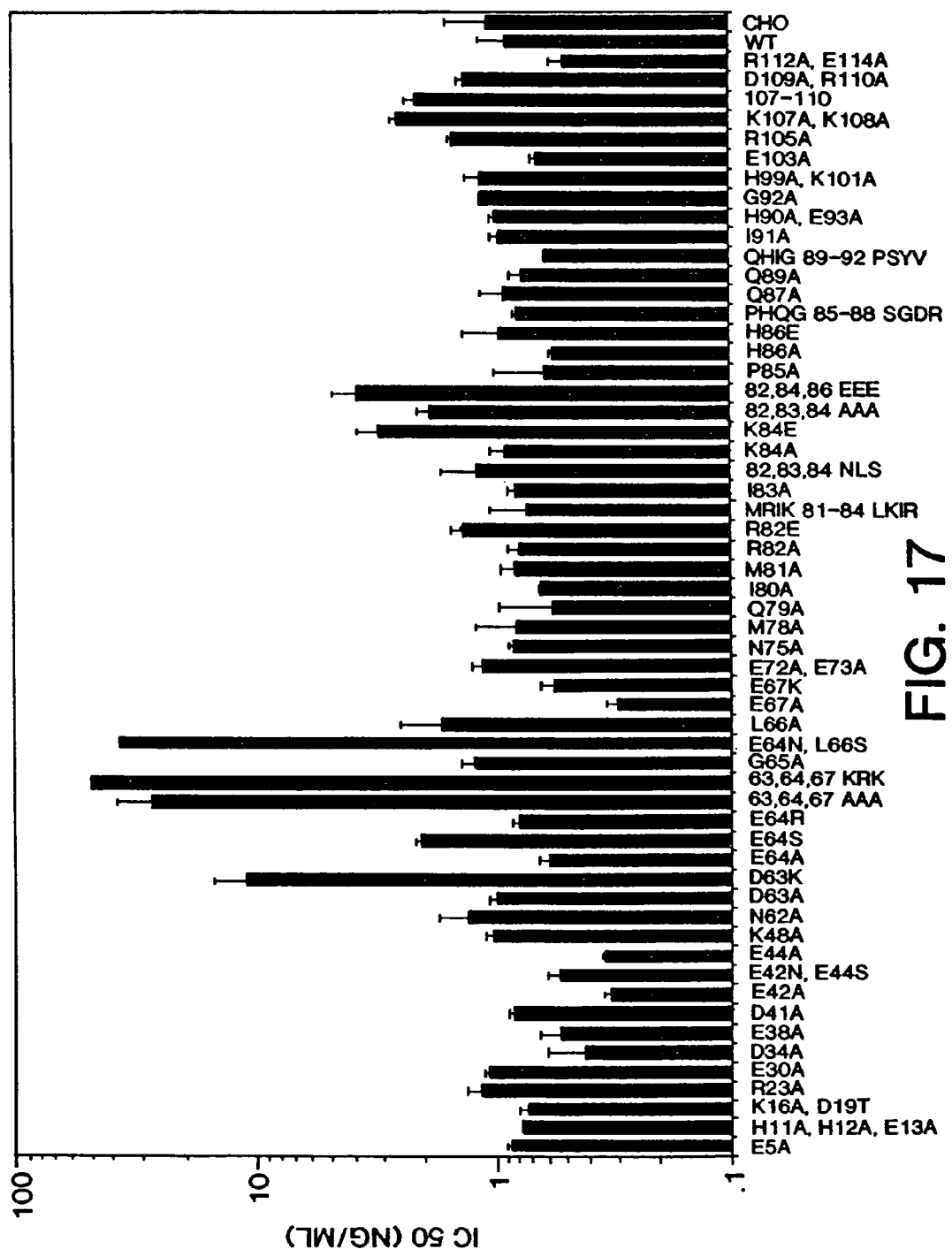
FIG. 17 depicts the FLT-1-IgG binding levels of various VEGF variants.
Figure 18:
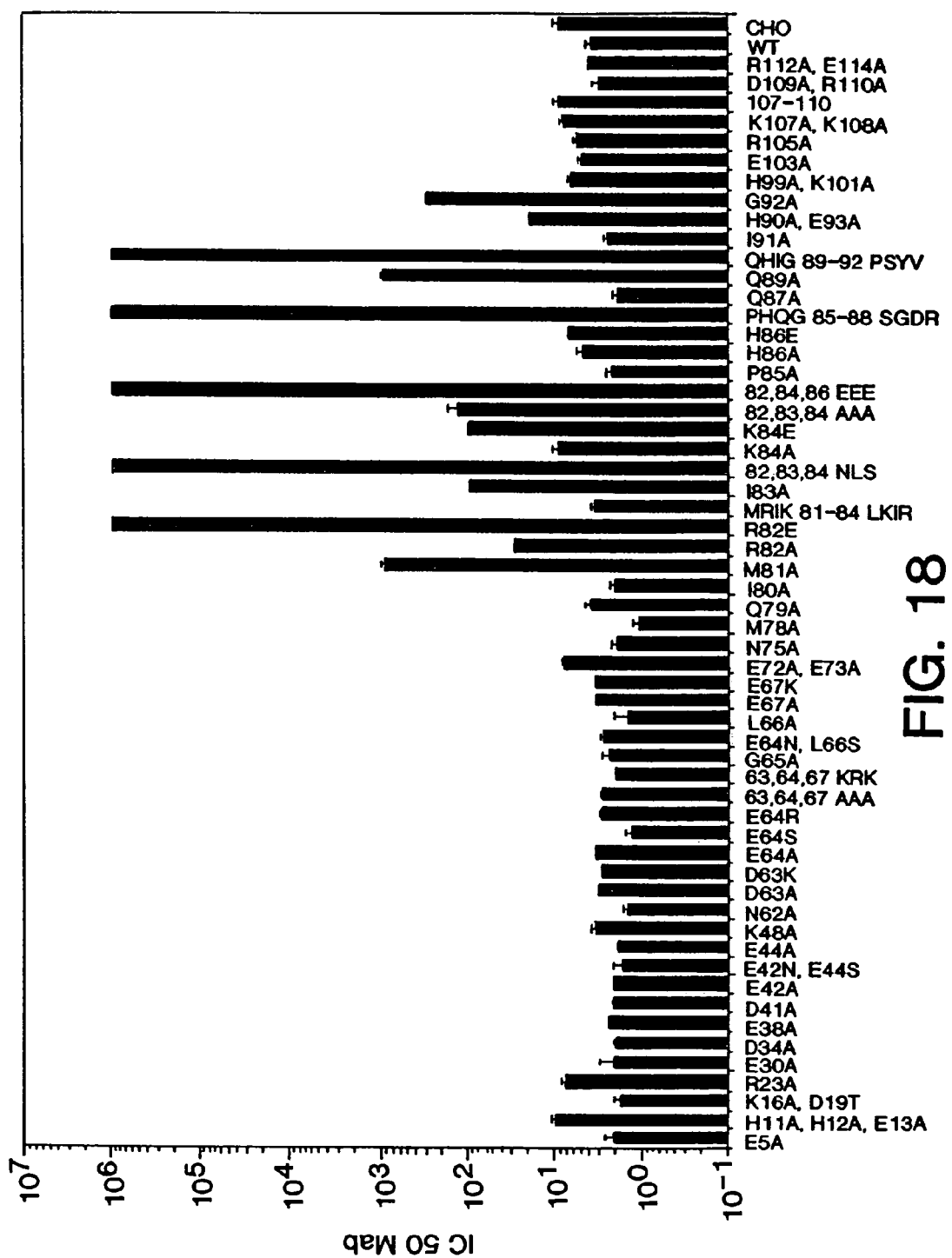
FIG. 18 depicts the A461-IgG binding levels of various VEGF variants.

It will be understood that one skilled in the art following the above details concerning the preparation of several mutants hereof can prepare yet other mutations to the VEGF molecule in accordance with the general parameters of the present invention as set forth in more detail supra. Attention is directed to FIGS. 16 to 18 where data on biological activities for a number of variants is provided.

Comparison of VEGF, PLGF and PDGF Sequences—Plasmin catalyses the cleavage of the carboxy-terminal, heparin-binding region (111-165) releasing the $VEGF_{110}$ dimer which displays bioactivity in the endothelial cell growth assay and in the Miles permeability assay [Houck et al., *J. Biol. Chem.* 267, 26031-26037 (1992)]. As such, we compared the sequence of the receptor binding region of VEGF (ie. 1-110) with sequences of homologous proteins, PLGF, PDGFa and PDGFb. The sequences were aligned with respect to the eight cysteines shared by this family of proteins. Six cysteines form intra-chain disulfides and two cysteines are inter-chain covalent linkages between monomers according to the homology with PDGFb [Haniu et al., *Biochemistry* 32, 2431-2437 (1993) and Pötgens et al., *J. Biol. Chem.* 269, 32879-32885 (1994)]. Two short gaps, inserted in the VEGF and PLGF sequences, are located at the apex of external loops based on the crystal structure of PDGFb dimer [Oefner et al., *The EMBO J.* 11, 3921-3926 (1992)]. $VEGF_{110}$ shares 47%, 15%, and 19% sequence identity and 63%, 24%, and 28% similarity with PLGF, PDGFa and PDGFb, respectively [George et al., *Meth. Enzymol.* 183, 333-351 (1990)]. Inspection of sequence similarity and divergence among these growth factors offers little insight as to the specific epitopes that mediate VEGF receptor binding. Functional mapping of VEGF was conducted by site-directed mutagenesis.

Figure 19:
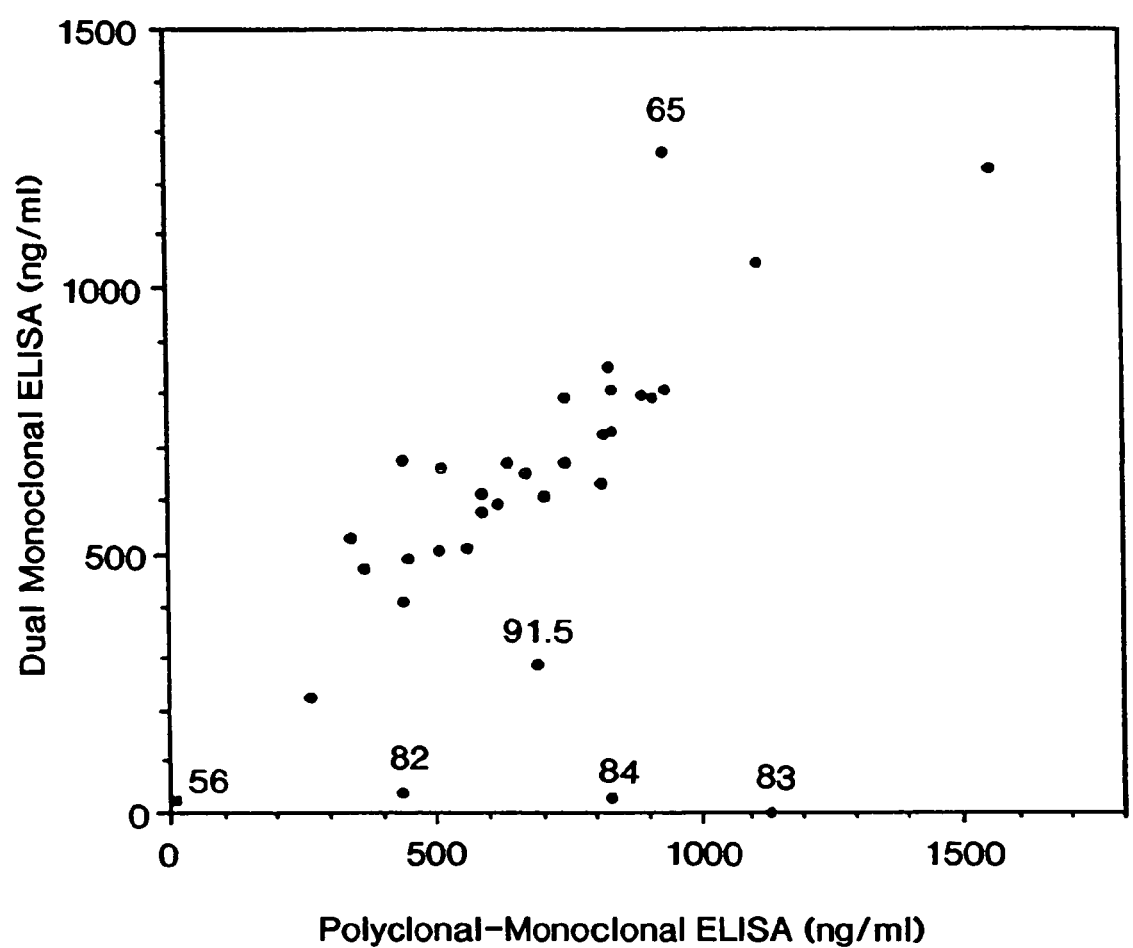
FIG. 19 shows the quantitation of VEGF mutants by monoclonal- and polyclonal-based ELISA. Aliquots of conditioned cell media with VEGF or VEGF mutants were analyzed by immunoassay using two types of ELISA. A polyclonal anti-VEGF antibody combined with a monoclonal antibody (Mab 5F8, specific to the carboxy-terminal domain of VEGF) yielded a sandwich-type immunoassay that was unaffected by mutations in the receptor-binding domain of VEGF (1-110 region). Alternatively, a dual monoclonal based ELISA with Mabs 5F8 and A4.6.1 was used to quantify the VEGF mutants. The immunoassay results of multiple transfections (2 to 10 replicates) were averaged for each mutant and compared in FIG. 19.

Clustered charged-to-alanine scan mutagenesis—Thirty mutants of $VEGF_{165}$ were constructed by site-directed mutagenesis where groups of between one and four neighboring charged amino acids (Arg, Lys, His, Asp, and Glu) were replaced with alanind (Table 6). Plasmid DNA encoding these mutants was transiently transfected in human 293 kidney cells and the amount of VEGF in the conditioned cell media was determined using two VEGF-specific immunochemical assays. In FIG. 19 the results of a polyclonal/monoclonal ELISA are compared to those obtained with a dual monoclonal assay. In the poly-/monoclonal assay, affinity purified polyclonal antibody reacted with multiple epitopes while the monoclonal antibody 5F8 is specific for determinants in the carboxy terminal, heparin-binding region (111-165) of VEGF. In contrast, the dual monoclonal ELISA utilized neutralizing and non-neutralizing monoclonal antibodies (Mabs A4.6.1 and 5F8, respectively). The use of two immunochemical detection methods assisted in the accurate determination of mutant VEGF concentration in conditioned cell media. For most VEGF mutants, the results of two immunochemical analyses were in good agreement, with transient expression levels ranging from 0.2 to 2 µg/ml of VEGF antigen in the conditioned media. Nearly all VEGF mutants were expressed with variable yield for repetitive transfections, with the notable exception of the R56A mutant of VEGF. No immunopositive protein was detected with the R56A mutation despite re-construction of the variant and numerous transfection attempts. It is interesting to note that arginine is strictly conserved at position 56 in VEGF, PLGF and PDGF, suggesting that this amino acid plays a vital role in structural integrity and/or native protein folding. Significantly, mutations in the region 82 to 86 were consistently underquantitated in the dual monoclonal ELISA compared to those results obtained with the poly-/monoclonal assay, indicating that the epitope recognized by the neutralizing monoclonal antibody, A4.6.1, includes this determinant in VEGF. The single amino acid substitution, R82A yields a mutant of VEGF exhibiting almost complete loss of immunochemical reactivity with Mab A4.6.1 (FIG. 19). Furthermore, VEGF mutations H90A, E93A displayed a partial loss of reactivity with Mab A4.6.1. These data suggest that the epitope of a neutralizing monoclonal antibody is localized to a region of VEGF including amino acids 82 to 93.

Non-Reducing, SDS-PA GE Analysis of VEGF Mutants—A representative set of transiently transfected supernatants (from 293 cells) containing approximately 10 to 20 ng of VEGF or VEGF mutant were analyzed by non-reducing SDS-PAGE. The gels were transferred and blotted as described above using a panel of 5 murine monoclonal anti-human $VEGF_{165}$ antibodies. Autoradiography of the immunoblots indicated a major band at 45 kDa for wildtype and mutant forms of VEGF. This immunopositive protein band co-migrated with purified, dimeric $VEGF_{185}$ derived from CHO cells. For some mutants of VEGF, and for 293 cell-derived wildtype VEGF (but not VEGF derived from CHO cells), there appeared an additional minor band at approximately 70 kDa. Apparent molecular weights for all alanine scan VEGF mutants, as indicated by SDS-PAGE, were equivalent to that observed for wildtype $VEGF_{165}$ derived from 293 or CHO cells. There was no indication of degraded forms of VEGF that would yield lower molecular weight species as has been observed for plasmin cleavage of VEGF [Houck et al., *J. Biol. Chem.* 267, 26031-26037 (1992) and Keyt et al., *The VIIIth International Symposium on the Biology of Vascular Cells*; Heidelberg, Germany, p. 48 (1994)].

Figure 6:
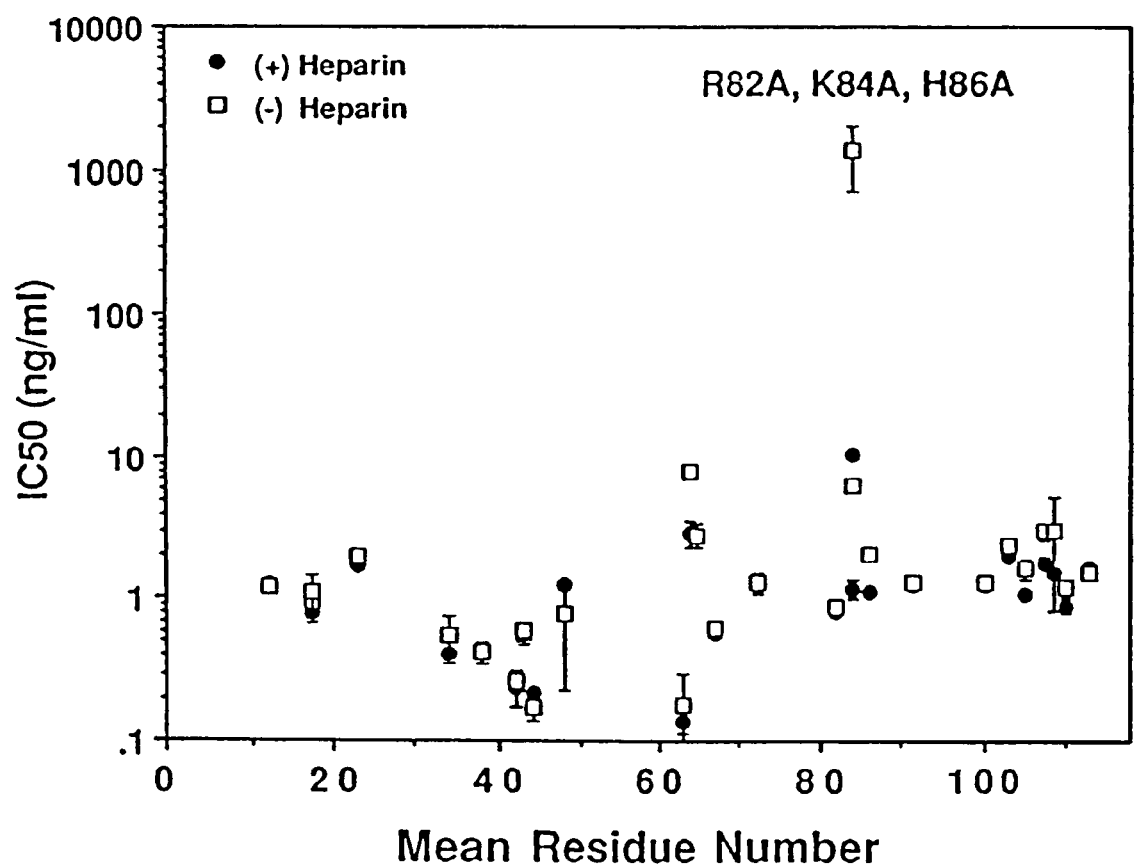
FIG. 6 shows that KDR-binding is primarily mediated by R82, K84, H86. IC50 refers to the 50% inhibitory concentration which is related to the disassociation constant.

VEGF Binding to KDR Receptor is Primarily Mediated by R82, K84, and H86—The binding of VEGF mutants to soluble KDR-IgG was evaluated by competitive displacement Of $^{125}I$ labeled $VEGF_{165}$ in the absence or presence of heparin. The list of mutations is given in Table 6. In addition to the specific amino acid substitutions, the table indicates the mean residue number for the position of the mutation(s). For a given mutant, this number is the average of the altered positions. The results for 27 charged-to-alanine scan mutants of VEGF in studies of binding to KDR-IgG are shown in FIG. 6, plotted with respect to the position of the mutation(s). Wildtype $VEGF_{165}$ expressed in 293 cells and CHO cells were equivalent with respect to displacement of $^{125}I$ labeled $VEGF_{165}$ in KDR binding. The concentrations required to achieve half-maximal inhibition ($IC_{50}$) were 31 pM and 29 pM for 293- or CHO-derived $VEGF_{165}$, respectively (n=8 replicates each). The $IC_{50}$ values for wildtype VEGF were not significantly different in the absence versus the presence of 15 µg/ml heparin.

Many of the mutant proteins exhibited binding comparable to wildtype VEGF. In fact, the binding to KDR for 19 out of 25 alanine scan mutants was similar to that of wildtype VEGF; the average $IC_{50}$ for mutants with wildtype-phenotype was 29±18 pM (n=19). However, the most significant effect on binding was observed with the R82A, K84A, H86A mutant of VEGF which exhibited 1000 fold decreased affinity for the KDR receptor in the absence of heparin, relative to that of wildtype VEGF (FIG. 6). Interestingly, in the presence of heparin the binding of this triple mutant was only 10 fold decreased compared to that of wildtype VEGF. These results are consistent with VEGF binding to KDR as a function of two sites of interaction, a heparin-independent site in the 1-110 dimer and a heparin dependent binding site in the 111-165 domain. In the absence of heparin, the binding of $VEGF_{165}$ to KDR is mediated entirely by the 1-110 region. Without heparin, the mutations at 82, 84 and 86 severely compromise the binding of VEGF to KDR. To evaluate the relative contribution of the individual residues, single amino acid substitution mutants of VEGF were constructed. The single mutations, R82A, K84A and H86A were found to display more modest decreases with respect to KDR binding in the absence of heparin (FIG. 10). R82A VEGF exhibited wildtype KDR binding, while K84A VEGF and H86A VEGF were approximately 5.5 fold and 2 fold decreased in binding compared to that of wildtype VEGF, respectively. All of the single alanine replacement mutants had normal binding affinity in the presence of heparin. While the 84 position of VEGF was most dominant in the triple alanine mutant, the combination of mutations at 82, 84 and 86 clearly exhibited a synergistic effect on the interaction with the KDR receptor.

In addition to the major KDR binding determinant, a minor site was observed in the 63 to 67 region. The triple mutant, D63A, E64A, E67A VEGF, was 3 fold reduced in binding to KDR in both the presence and absence of heparin. Single amino acid mutations in this region displayed different characteristics. Wildtype-like binding to KDR was observed for D63A VEGF and E67A VEGF. In contrast, E64A VEGF had 8 fold and 3 fold decreased binding in the absence and presence of heparin, respectively. Although modest in comparison to the major effects observed with R82A, K84A, H86 VEGF, the most potent effects with single alanine replacement of charged amino acids were observed for E64A VEGF and K84A VEGF.

Figure 7:
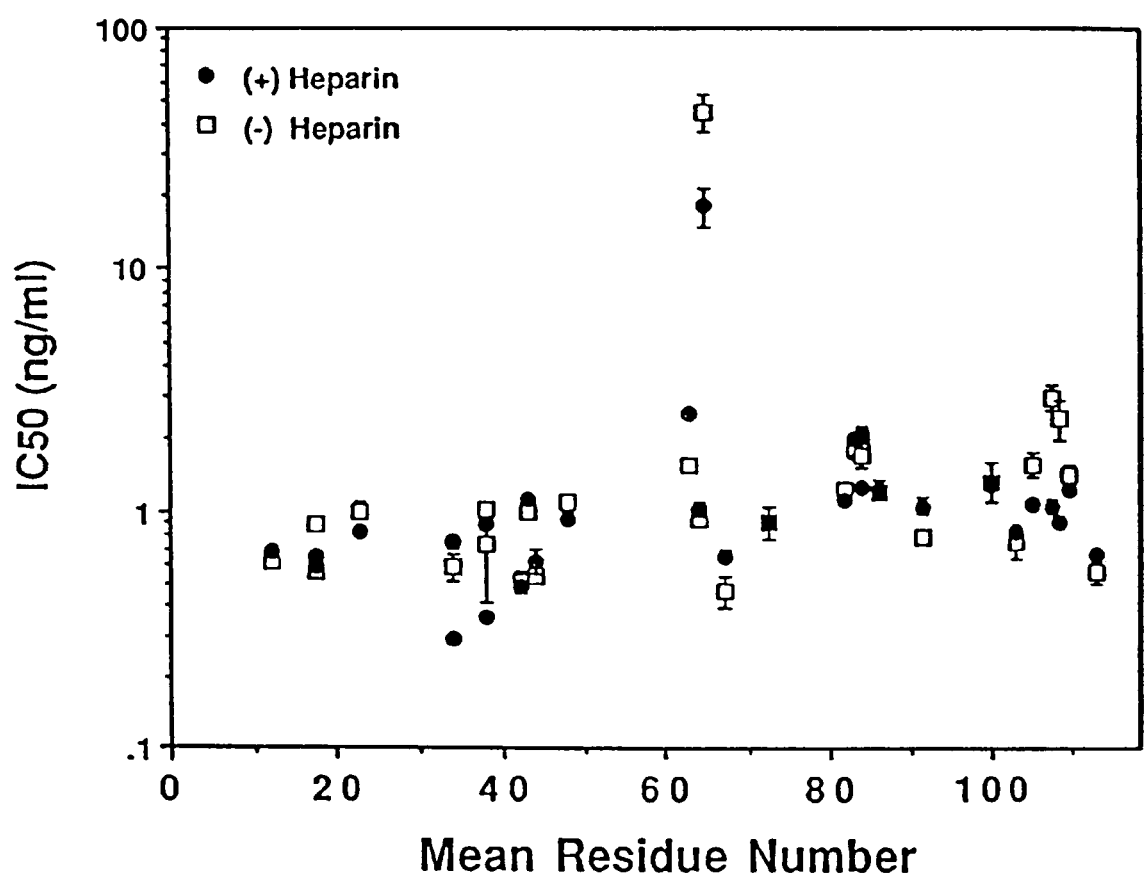
FIG. 7 shows that FLT-binding is primarily mediated by D63, E64, E67.
Figure 8:
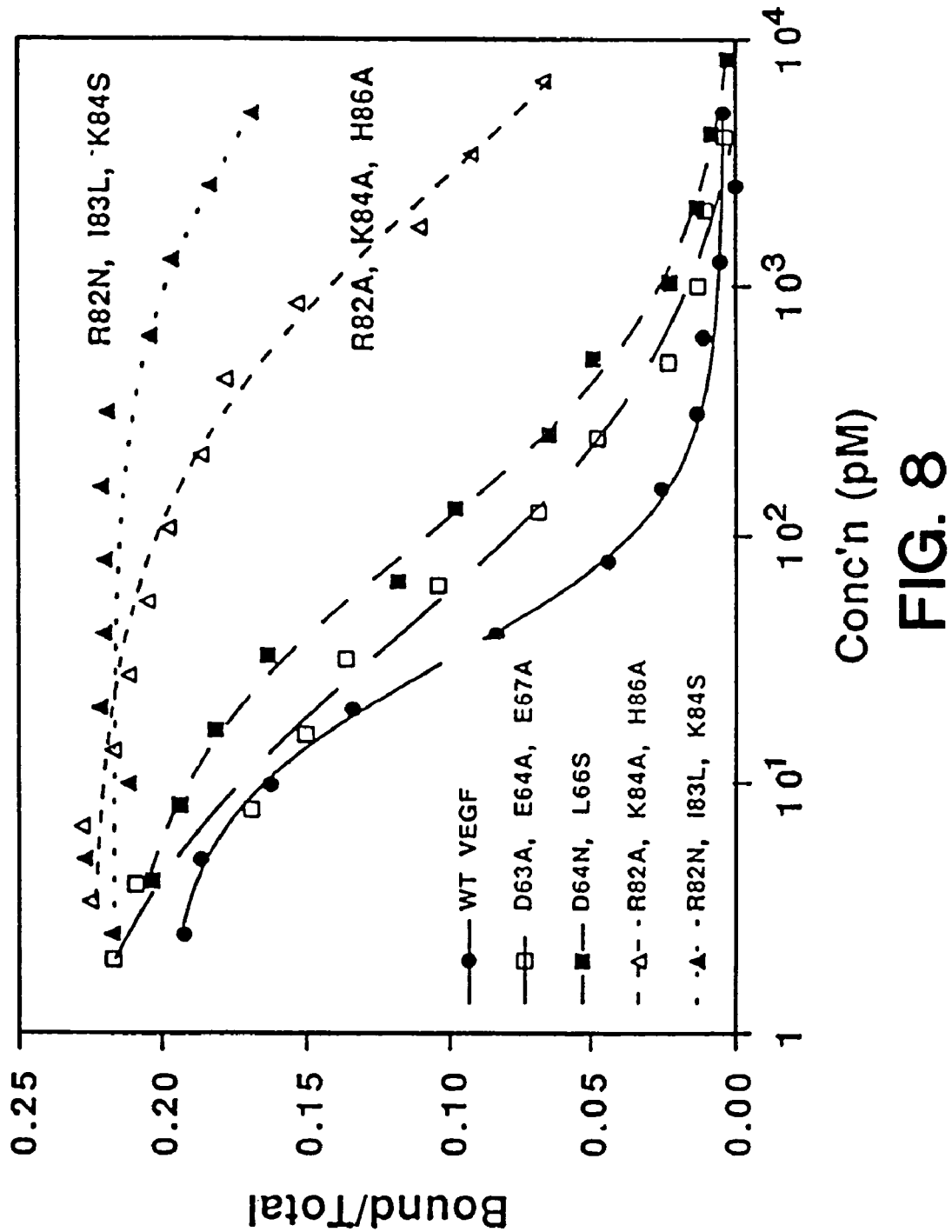
FIG. 8 shows that extra glycosylation at position 82 blocks KDR-binding.

VEGF Binding to FLT-1 Receptor Involves Interaction with D63, E64, and E67 As was observed for KDR binding, most of the alanine scan mutants of VEGF bound FLT-1 with similar affinity as wildtype VEGF (FIG. 7). Compared to KDR, there appeared less effect of heparin on the FLT-1 binding of wildtype VEGF or the majority of mutants which displayed wildtype-phenotypic binding to FLT-1. The $IC_{50}$ values for wildtype VEGF were 22±8 and 15±8 in the absence and presence of heparin, respectively (n=13). Analysis of alanine scan VEGF mutants indicated two sites of interaction with FLT-1 that co-localized with the KDR binding determinants. A major site for FLT-1 binding involves the 63 to 67 region of VEGF as indicated by the approximately 30 fold reduction in affinity with D63A, E64A, E67A VEGF in the absence of heparin. This is in contrast to the results with KDR which indicated mutations in the 63-67 region of VEGF exhibited only modest effects on KDR binding. In the presence of heparin, D63A, E64A, E67A VEGF binding to FLT-1 was decreased about 20 fold compared to wildtype VEGF. The major site of KDR interaction (82-86 region) yielded only minor effects with respect to FLT-1 binding. R82A, K84A, H86A VEGF was slightly reduced in binding to FLT-1 in the presence or absence of heparin. Additional mutational sites at the carboxy terminus were associated with minor effects on FLT-1 binding. Interestingly, the major site mediating KDR interaction, that was localized to 82 to 86 region of VEGF, exhibited only a modest effect on FLT-1 binding. In contrast, the major site for FLT-1 binding was localized to the 63-67 region of VEGF, which displayed minor effects on KDR binding. The relative roles of major and minor receptor binding sites are reversed for FLT-1 in comparison to that for KDR.

The Effect of Glycosylation on Receptor Binding—We altered the glycosylation sites of VEGF to confirm and extend the results observed with alanine scanning mutagenesis. First, the role of a single putative site of N-linked glycosylation at position 75 was evaluated for VEGF. An unglycosylated form of VEGF was constructed, expressed in 293 cells and visualized by SDS-PAGE and immunoblotting (FIG. 20). This mutant, N75A VEGF, appeared to have a lower molecular weight consistent with the lack of glycosylation at position 75, and by inference, this result confirms that wildtype VEGF expressed in 293 cells does contain N-linked carbohydrate at that site. The binding of N75A VEGF was indistinguishable from that of wildtype VEGF for both KDR and FLT-1 soluble receptors in the presence and absence of heparin. For the wildtype protein, N-linked carbohydrate at $Asn^{75}$ does not appear to play a role in mediating VEGF receptor binding.

Potential neo-glycosylation sites were inserted at three novel sites in VEGF to observe the effects of carbohydrate addition at or near the putative site of receptor binding. Surface accessible sites were considered optimal in exterior loops or turns as predicted on the basis of the crystal structure of PDGFb dimer [Oefner et al., *The EMBO J.* 11, 3921-3926 (1992)]. One such site (42-44 region) was selected as a control since no receptor binding determinants were identified in this region by charged-to-alanine scanning mutagenesis. The neocarbohydrate site in E42N, E44S VEGF was apparently glycosylated as indicated by the increased molecular weight observed on SDS-PAGE immunoblots (FIG. 20). The N-linked carbohydrate at position 42 did not interfere with binding to KDR or FLT-1 receptors as indicated by $IC_{50}$ values of 15 pM and 13 pM, respectively.

Figure 9A:
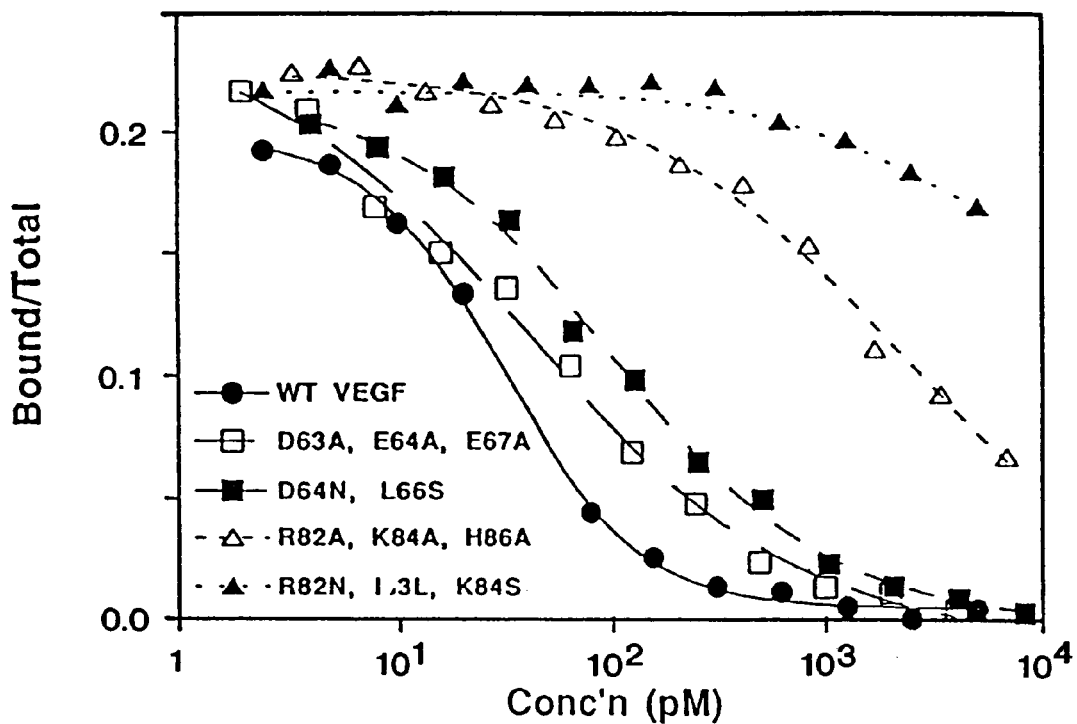
FIG. 9 shows that mutations in the 82-86 site block KDR-binding (A) and that mutations in the 63-67 site block FLT-binding (B).
Figure 9B:
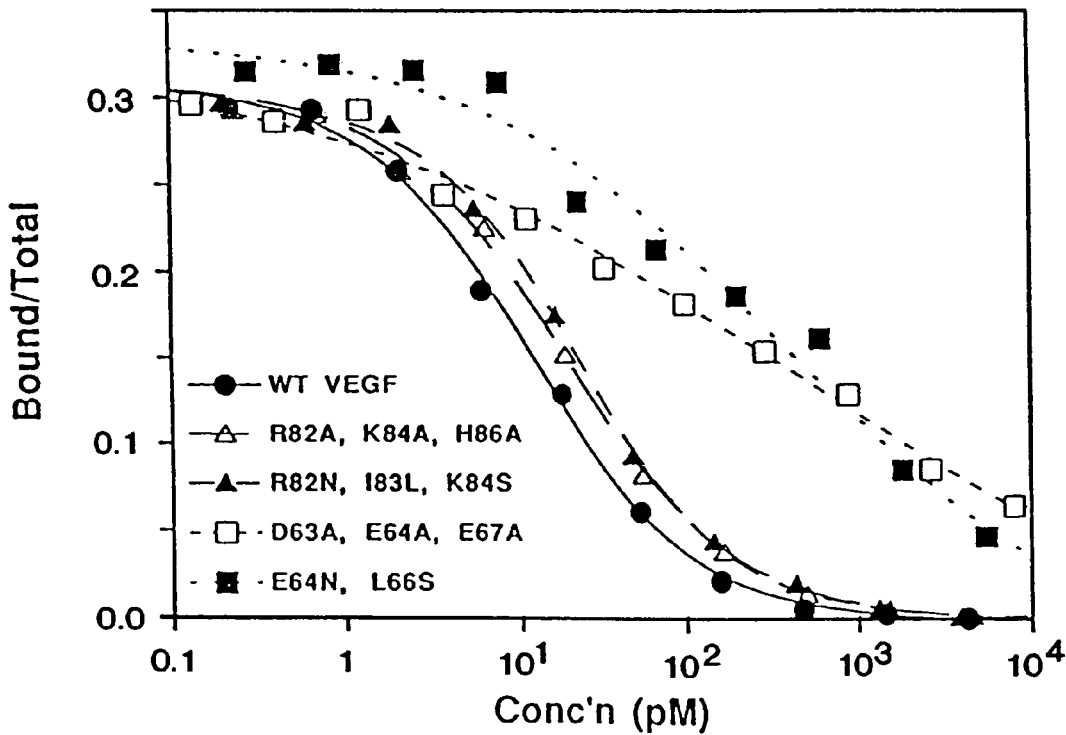

Potential Glycosylation Site at Position 82 Results in Severely Decreased KDR Binding—Mutations of VEGF in the KDR binding site introduced a novel potential N-linked glycosylation site at position 82. RIK(82-84)NLS VEGF was constructed, expressed in 293 cells and evaluated by SDS-PAGE immunoblotting (FIG. 20). The extent of additional glycosylation at Asn82 was not apparent on the immunoblot for RIK(82-84)NLS VEGF as compared to the change in electrophoretic mobility observed with E42N, E44S VEGF. Although the RIK(82-84)NLS mutation had little effect on apparent molecular weight, the effect on KDR binding was quite significant. RIK(82-84)NLS VEGF exhibited only partial displacement of the labeled VEGF in KDR binding assays in the absence of heparin (FIG. 9A). The half-maximal inhibitory concentration for RIK(82-84)NLS VEGF was estimated to be 10,000 fold greater than that observed for wildtype VEGF. This mutant which exhibited virtually no affinity for soluble KDR in the absence of heparin, was capable of full displacement of VEGF in the presence of heparin, albeit at higher concentrations. The relative affinity of RIK(82-84) NLS VEGF for KDR was 50 fold decreased compared to that of wildtype VEGF with 15 µg/ml heparin. Interestingly, this putative extra-glycosylation mutation resulted in a mutant exhibiting normal affinity for FLT-1 (FIG. 9B). RIK(82-84) NLS VEGF and wildtype VEGF displayed similar FLT-1 binding affinity in the presence and absence of heparin. Mutations in the 82 to 86 region (R82A, K84A, H86A and RIK (82-84)NLS) confer significantly decreased interaction with KDR and normal binding to FLT-1. As such, RIK(82-84)NLS VEGF is a highly FLT-1 selective variant of VEGF.

Extra-glycosylation Site Mutant at Position 64 Decreases FLT-1, but not KDR Binding—A VEGF mutant was designed to introduce a neo-glycosylation site in the region (63-67) which has been shown to mediate FLT-1 binding. E64N, L66S VEGF was constructed, expressed in 293 cells and evaluated by immunoblotting for evidence of glycosylation. E64N, L66S VEGF was observed as a faint band with apparent increased molecular weight on SDS-PAGE (FIG. 20). The binding studies indicated that E64N, L66S VEGF was 40 fold reduced in FLT-1 binding in the absence of heparin (FIG. 9B). In contrast to the results observed with KDR-specific mutations in the 82-86 region, the putative extra-glycosylation mutant (E64N, L66S VEGF) displayed similar FLT-1 binding affinity as the triple mutant of VEGF (D63A, E64A, E67A). As with the corresponding triple mutant, E64N, L66S VEGF exhibited little change in the binding to FLT-1 depending on the presence versus the absence of heparin ($IC_{50}$: 650 pM versus 980 pM, respectively). The mutants having FLT-1 specific effects exhibited modestly decreased binding with KDR receptor. The relative binding of D63A, E64A, E67A VEGF and E64N, L66S VEGF to soluble KDR was approximately 3 fold and 6 fold decreased, respectively. The mutations in the 63-67 region of VEGF confer KDR selectivity in that these mutants bind KDR similar to wildtype VEGF, but FLT-1 binding is decreased.

Figure 11:
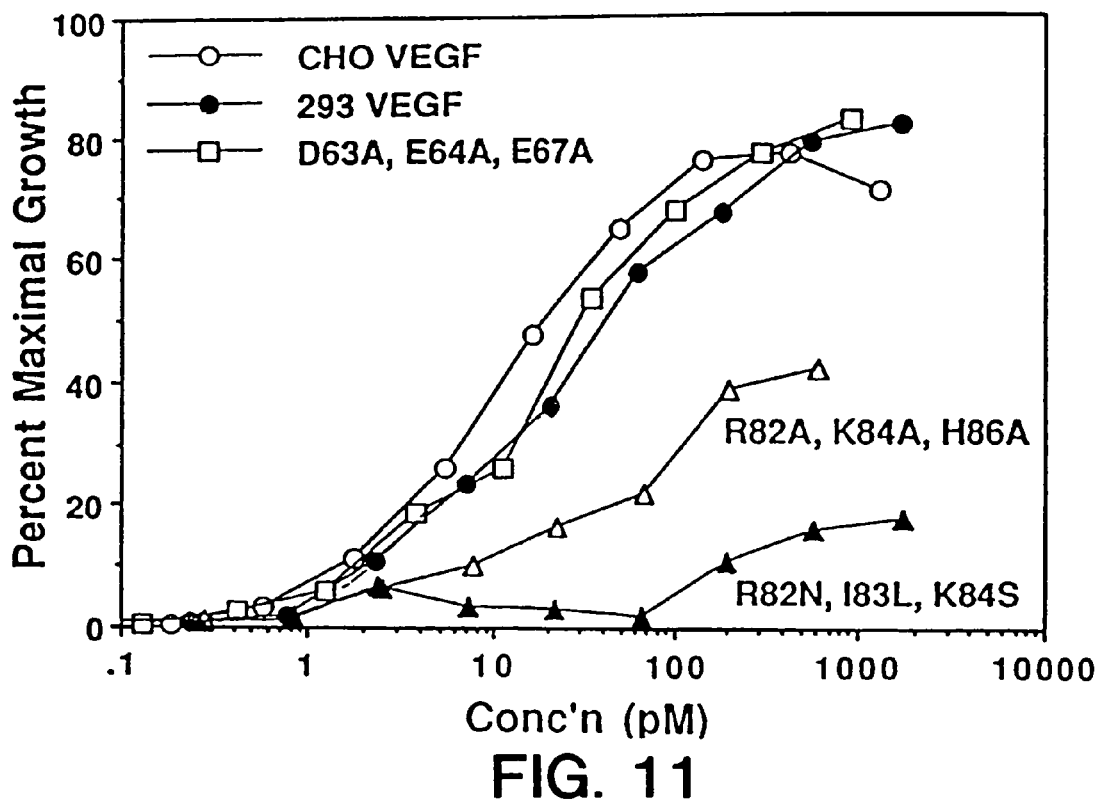
FIG. 11 shows that VEGF mutants with decreased KDR receptor binding are weak endothelial cell mitogens.
Figure 12:
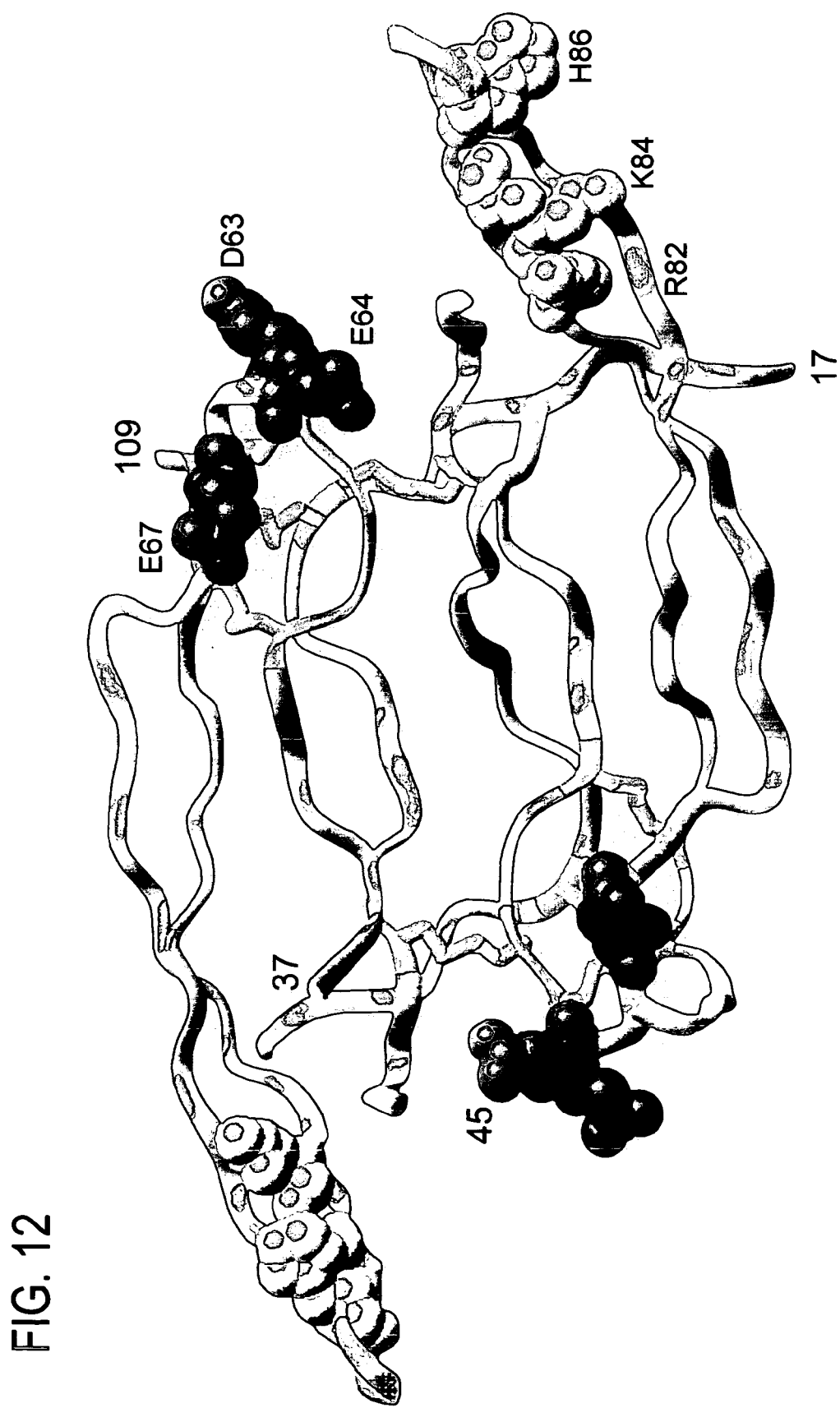
FIG. 12 is a color photograph of a molecular model of VEGF showing the locations of the KDR-(blue) and FLT-(red) binding sites.

VEGF Mutants with Decreased KDR Receptor Binding are Weak Endothelial Cell Mitogens—Mitogenic activities of VEGF and mutants of VEGF were determined using bovine adrenal cortical capillary endothelial cells. Wildtype VEGF, derived from 293 cells or CHO cells, induced half maximal proliferation at 28±10 pM (n=6) and 16±8 pM (n=9), respectively. Conditioned cell media from mock transfected 293 cells did not induce endothelial cell proliferation. The half-maximally effective concentrations ($EC_{50}$) for most of the VEGF mutants were similar to those observed for wildtype VEGF (FIG. 21). The most significant effect on endothelial cell proliferation was observed with mutations in the 82-86 region. The $EC_{50}$ of R82A, K84A, H86A VEGF increased to 520±150 pM (n=4) such that mitogenic potency of this mutant was decreased to 5% of wildtype VEGF. To confirm and extend this observation, the neo-glycosylation site mutant was also evaluated for its relative mitogenic potency. Induction of proliferation by RIK(82-84)NLS VEGF was reduced to such an extent that wildtype-VEGF level growth was not achieved at the highest concentration tested (FIG. 11). To quantitatively assess the potency of RIK(82-84)NLS VEGF, we compared the concentration of the mutant required to achieve 20% of maximal VEGF-induced stimulation. The difference in $EC_{20}$ values for wildtype VEGF and RIK(82-84)NLS VEGF (4 pM versus 230 pM, respectively) indicated 60 fold reduced potency for the mutant with a neo-glycosylation site in the region specific for KDR binding. The effect of these mutations on endothelial cell growth is consistent with the KDR binding data. The affinity of R82A, K84A, H86A VEGF and RIK(82-84)NLS VEGF with soluble KDR (in the presence of heparin) was reduced 10 fold and 50 fold, respectively, compared to that observed with wildtype VEGF. Since endothelial cells in vitro express surface and matrix associated heparin sulfates [Barzu et al., *Biochim. Biophys. Acta.* 845, 196-203 (1985)], it is appropriate to compare the mitogenic response of endothelial cells to VEGF or VEGF mutants with the binding data for those proteins to soluble VEGF receptors in the presence of heparin. Taken together, the mutational analysis of VEGF by alanine scanning and extra-glycosylation provide strong evidence that binding to KDR receptors on endothelial cells is a triggering event for the induction of proliferation observed with VEGF.

VEGF Mutants with Decreased FLT-1 Receptor Binding are Fully Active Endothelial Cell Mitogens—Alanine scan substitutions in the 63-67 region of VEGF were shown to have normal binding to KDR and decreased binding to FLT-1 (FIGS. 6 and 9). Triple and single alanine mutants (D63A, E64A, E67A VEGF, D63A VEGF, E64A VEGF, and E67A VEGF) were evaluated for induction of endothelial cell growth. All of these mutants exhibited mitogenic potency similar to that of wildtype VEGF (FIGS. 21 and 11). The mutant with a putative extra-glycosylation site in the 63-67 region; E64N, L66S VEGF also exhibited normal activity on endothelial cells (FIG. 21). These data reinforce the observation that FLT-1 deficient mutants of VEGF induce endothelial cell proliferation similar to wildtype VEGF. Furthermore, these data suggest that VEGF binding to FLT-1 receptors on endothelial cells is unrelated to mitogenesis and proliferation. This mutational analysis has identified VEGF variants that are relatively selective for KDR or FLT-1 receptors. The data in this report suggests an electrostatic component of VEGF: receptor interaction, such that the determinants for KDR and FLT-1 include predominantly positive or negatively charged regions of VEGF, respectively.

Concluding Remarks:

The foregoing description details specific methods which can be employed to practice the present invention. Having detailed such specific methods, those skilled in the art will well enough know how to devise alternative reliable methods at arriving at the same information in using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

The invention claimed is:

1. A method for stimulating vasculogenesis or angiogenesis, comprising contacting endothelial cells with a vascular endothelial cell growth factor (VEGF) having decreased binding affinity for FLT-1 receptor due to one or more amino acid substitutions in the FLT-1 binding region compared to wildtype VEGF, wherein the substituted VEGF stimulates vasculogenesis or angiogenesis.

2. The method of claim 1, wherein the substituted VEGF exhibits increased binding affinity for KDR as compared to the binding affinity of the VEGF without said substitution(s) for KDR.

3. The method of claim 1, wherein the substituted VEGF exhibits a higher KDR to FLT-1 binding ratio as compared with the VEGF without said substitution(s).

4. The method of claim 1, wherein the amino acid substitution is non-conservative.

5. The method of claim 1, wherein the FLT-1 region corresponds to amino acids 60 to 70 of wildtype VEGF.

6. The method of claim 5, wherein the native VEGF is wildtype human $VEGF_{165}$.

7. The method of claim 1, wherein one or more of amino acids 63, 64, or 67 of wildtype VEGF are substituted.

8. The method of claim 7, wherein the amino acid substitution comprises D63A, E64A, and E67A.

9. The method of claim 7, wherein the amino acid substitution comprises D63K.

10. The method of claim 7, wherein the amino acid substitution comprises D63K, E64R, and E 67K.

11. The method of claim 7, wherein the amino acid substitution comprises E64N and L66S.

12. The method of claim 1, wherein the endothelial cells expresses KDR receptor.

13. A method for stimulating proliferation of an endothelial cell, comprising contacting the endothelial cells with an effective amount of a vascular endothelial cell growth factor (VEGF) having decreased binding affinity for FLT-1 receptor due to one or more amino acid substitutions in the FLT-1 binding region compared to wildtype VEGF, wherein the substituted VEGF stimulates proliferation of an endothelial cell.

14. A method of treating trauma to a vascular network in a mammal, comprising administering to the mammal a vascular endothelial cell growth factor (VEGF) having decreased binding affinity for FLT-1 receptor due to one or more non-conservative amino acid substitutions in the FLT-1 binding region compared to wildtype VEGF, wherein the substituted VEGF stimulates endothelial cell proliferation, vasculogenesis, or angiogenesis.

15. The method of claim 14, wherein the trauma is a wound.

16. The method of claim 15, wherein the wound is a laceration, incision, or penetration of blood vessels.

17. The method of claim 16, wherein the incision is a surgical incision.

18. The method of claim 16, wherein the trauma is an ulcer.

19. The method of claim 18, wherein the ulcer is a diabetic, hemophiliac, or varicose ulcer.

* * * * *

UNITED STATES PATENT AND TRADEMARK OFFICE
CERTIFICATE OF CORRECTION

PATENT NO.           : 7,427,596 B2                                          Page 1 of 1
APPLICATION NO.  : 11/145494
DATED                   : September 23, 2008
INVENTOR(S)         : Bruce Keyt et al.

It is certified that error appears in the above-identified patent and that said Letters Patent is hereby corrected as shown below:

Column 53, Claim 6, Line 39 "native" should read --wildtype--

Signed and Sealed this

Eighth Day of September, 2009

David J. Kappos
*Director of the United States Patent and Trademark Office*

SEQUENCE LISTING

<160> NUMBER OF SEQ ID NOS: 42

<210> SEQ ID NO 1
<211> LENGTH: 990
<212> TYPE: DNA
<213> ORGANISM: Bovine
<220> FEATURE:
<221> NAME/KEY: CDS
<222> LOCATION: (57)..(632)

<400> SEQUENCE: 1

```
cagtgtgctg gcggcccggc gcgagccggc ccggccccgg tcgggcctcc gaaacc atg      59
                                                                 Met
                                                                   1 aac ttt ctg ctg tct tgg gtg cat tgg agc ctc gcc ttg ctg ctc tac        107
Asn Phe Leu Leu Ser Trp Val His Trp Ser Leu Ala Leu Leu Leu Tyr
        5                   10                  15 ctc cac cat gcc aag tgg tcc cag gct gca ccc atg gca gaa gga gga        155
Leu His His Ala Lys Trp Ser Gln Ala Ala Pro Met Ala Glu Gly Gly
     20                  25                  30 ggg cag aat cat cac gaa gtg gtg aag ttc atg gat gtc tat cag cgc        203
Gly Gln Asn His His Glu Val Val Lys Phe Met Asp Val Tyr Gln Arg
 35                  40                  45 agc tac tgc cat cca atc gag acc ctg gtg gac atc ttc cag gag tac        251
Ser Tyr Cys His Pro Ile Glu Thr Leu Val Asp Ile Phe Gln Glu Tyr
 50                  55                  60                  65
```

-continued

```
cct gat gag atc gag tac atc ttc aag cca tcc tgt gtg ccc ctg atg      299
Pro Asp Glu Ile Glu Tyr Ile Phe Lys Pro Ser Cys Val Pro Leu Met
             70                  75                  80 cga tgc ggg ggc tgc tgc aat gac gag ggc ctg gag tgt gtg ccc act      347
Arg Cys Gly Gly Cys Cys Asn Asp Glu Gly Leu Glu Cys Val Pro Thr
                 85                  90                  95 gag gag tcc aac atc acc atg cag att atg cgg atc aaa cct cac caa      395
Glu Glu Ser Asn Ile Thr Met Gln Ile Met Arg Ile Lys Pro His Gln
                100                 105                 110 ggc cag cac ata gga gag atg agc ttc cta cag cac aac aaa tgt gaa      443
Gly Gln His Ile Gly Glu Met Ser Phe Leu Gln His Asn Lys Cys Glu
            115                 120                 125 tgc aga cca aag aaa gat aga gca aga caa gaa aat ccc tgt ggg cct      491
Cys Arg Pro Lys Lys Asp Arg Ala Arg Gln Glu Asn Pro Cys Gly Pro
130                 135                 140                 145 tgc tca gag cgg aga aag cat ttg ttt gta caa gat ccg cag acg tgt      539
Cys Ser Glu Arg Arg Lys His Leu Phe Val Gln Asp Pro Gln Thr Cys
                150                 155                 160 aaa tgt tcc tgc aaa aac aca gac tcg cgt tgc aag gcg agg cag ctt      587
Lys Cys Ser Cys Lys Asn Thr Asp Ser Arg Cys Lys Ala Arg Gln Leu
                165                 170                 175 gag tta aac gaa cgt act tgc aga tgt gac aag ccg agg cgg tga          632
Glu Leu Asn Glu Arg Thr Cys Arg Cys Asp Lys Pro Arg Arg
            180                 185                 190 gccgggcagg aggaaggagc ctccctcagg gtttcgggaa ccagatctct caccaggaaa    692
gactgataca gaacgatcga tacagaaacc acgctgccgc caccacacca tcaccatcga    752
cagaacagtc cttaatccag aaacctgaaa tgaaggaaga ggagactctg cgcagagcac    812
tttgggtccg gagggcgaga ctccggcgga agcattcccg ggcgggtgac ccagcacggt    872
ccctcttgga attggattcg ccattttatt tttcttgctg ctaaatcacc gagcccggaa    932
gattagagag ttttatttct gggattcctg tagacacacc gcggccgcca gcacactg     990
```

<210> SEQ ID NO 2
<211> LENGTH: 191
<212> TYPE: PRT
<213> ORGANISM: Bovine

<400> SEQUENCE: 2

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
     50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140
```

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

```
<210> SEQ ID NO 3
<211> LENGTH: 59
<212> TYPE: DNA
<213> ORGANISM: Artificial Sequence
<220> FEATURE:
<223> OTHER INFORMATION: Description of Artificial Sequence: Synthetic.

<400> SEQUENCE: 3
cctatggctg aaggcggcca gaagcctcac gaagtggtga agttcatgga cgtgtatca      59

<210> SEQ ID NO 4
<211> LENGTH: 99
<212> TYPE: DNA
<213> ORGANISM: Artificial Sequence
<220> FEATURE:
<223> OTHER INFORMATION: Description of Artificial Sequence: Synthetic.

<400> SEQUENCE: 4
agtagcaagc ttgacgtgtg gcaggcttga gatctggcca tacacttgag tgacaatgac      60
atccactttg cctttctctc cacaggtgtc cactcccag                             99

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic.

<400> SEQUENCE: 5
aggctgctgc agttcgacgt gggagtggac                                       30

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 6
ccctcctccg gctgccatgg gtgc                                             24

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic.

<400> SEQUENCE: 7
cttcaccacg gcggcggcat tctgccctcc                                       30

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic.
```

```
<400> SEQUENCE: 8
ctgatagacg gccatgaagg ccaccacttc gtg                              33

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 9
gcagtagctg gcctgataga catc                                        24

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic.

<400> SEQUENCE: 10
caccagggtg gcgattgggg cgcagtagct gcg                              33

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic.

<400> SEQUENCE: 11
atcagggtag gcctggaaga tggccaccag ggtctc                           36

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic.

<400> SEQUENCE: 12
gaagatgtag gcgatggcgg cagggtactc ctg                              33

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 13
acaggatggg gcgaagatgt actc                                        24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 14
gcccccgcag gccatcaggg gcac                                        24

<210> SEQ ID NO 15
```

```
<211> LENGTH: 36
<212> TYPE: DNA
<213> ORGANISM: Artificial Sequence
<220> FEATURE:
<223> OTHER INFORMATION: Description of Artificial Sequence: Synthetic.

<400> SEQUENCE: 15
gggcacacag gccaggccgg cggcattgca gcagcc                              36

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 16
gatgttggag gcggcagtgg gcacaca                                        27

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic.

<400> SEQUENCE: 17
ctggccttgg gcaggggcga tggccataat ctgcat                              36

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic.

<400> SEQUENCE: 18
gaagctcatg gctcctatgg cctggccttg gtg                                 33

<210> SEQ ID NO 19
<211> LENGTH: 30
<212> TYPE: DNA
<213> ORGANISM: Artificial Sequence
<220> FEATURE:
<223> OTHER INFORMATION: Description of Artificial Sequence: Synthetic.

<400> SEQUENCE: 19
gcattcacag gcgttggcct gtaggaagct                                     30

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 20
tggtctgcag gcacatttgt tgtg                                           24

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic.

<400> SEQUENCE: 21
```
ttgtcttgcg gcggcggcgg ctggtctgca ttc       33

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 22
tgctctatcg gcggctggtc tgcattc       27

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 23
ttgtcttgcg gcggctttct ttggtct       27

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 24
tttctttggg gcgcattcac attt       24

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic.

<400> SEQUENCE: 25
acagggattg gcttgggctg ctctatcttt       30

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 26
catggtgatg gcggactcct cagt       24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 27
caccacttcg gtatgattct gccc       24

<210> SEQ ID NO 28
<211> LENGTH: 24
<212> TYPE: DNA

<213> ORGANISM: Artificial Sequence
<220> FEATURE:
<223> OTHER INFORMATION: Description of Artificial Sequence: Synthetic.

<400> SEQUENCE: 28
ctccaggccg gtgtcattgc agca					24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 29
gcaacgcgag gttgtgtttt tgca					24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic.

<400> SEQUENCE: 30
tctgcaagtg gtttcgttta actc					24

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 31
caccacttcg tgggcattct gccctcc					27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 32
cttcaccact tcggcatgat tctgccc					27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 33
gaacttcacc acggcgtgat gattctg					27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 34
gacatccatg aaggccacca cttcgtg					27

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic.

<400> SEQUENCE: 35
gcgctgatag acggccatga acttcaccac                                    30

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 36
ggtctcgatt ggggcgcagt agctgcg                                       27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 37
ctcctggaag atggccacca gggtctc                                       27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 38
ctcatcaggg taggcctgga agatgtc                                       27

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 39
gtaatcgatc tcggcagggt actcctg                                       27

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 40
gtccaccagg gtggcgattg gatggca                                       27

<210> SEQ ID NO 41
<211> LENGTH: 27
<212> TYPE: DNA
<213> ORGANISM: Artificial Sequence
<220> FEATURE:

```
<223> OTHER INFORMATION: Description of Artificial Sequence: Synthetic.

<400> SEQUENCE: 41
gatgtactcg atggcatcag ggtactc                                    27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic.

<400> SEQUENCE: 42
cttgaagatg taggcgatct catccag                                    27
```